(12) United States Patent
Hanson et al.

(10) Patent No.: US 8,857,279 B2
(45) Date of Patent: Oct. 14, 2014

(54) ANALYTE SCREENING AND DETECTION SYSTEMS AND METHODS

(76) Inventors: William P. Hanson, Carlisle, PA (US); Maureen A. Dyer, Mechanicsburg, PA (US); Robert E. Hetrick, Loysville, PA (US); Jennifer A. Oberholtzer, Mechanicsburg, PA (US)

(*) Notice: Subject to any disclaimer, the term of this patent is extended or adjusted under 35 U.S.C. 154(b) by 1046 days.

(21) Appl. No.: 12/041,660

(22) Filed: Mar. 3, 2008

(65) Prior Publication Data

US 2009/0217777 A1 Sep. 3, 2009

(51) Int. Cl.
| | |
|---|---|
| *G01N 1/20* | (2006.01) |
| *C02F 1/44* | (2006.01) |
| *G01N 1/40* | (2006.01) |
| *B01D 61/14* | (2006.01) |
| *B01D 61/18* | (2006.01) |
| *C40B 60/12* | (2006.01) |

(52) U.S. Cl.
CPC ............ *G01N 1/4077* (2013.01); *B01D 61/145* (2013.01); *B01D 61/18* (2013.01); *B01D 2311/13* (2013.01); *G01N 2001/4088* (2013.01); *C40B 60/12* (2013.01)
USPC ........ 73/863.23; 210/636; 210/651; 210/797; 73/61.72

(58) Field of Classification Search
CPC ................... G01N 1/4077; G01N 2011/4088; B01D 2311/13; B01D 61/145; B01D 61/18; C40B 60/12
USPC ....................................................... 435/5, 6
See application file for complete search history.

(56) References Cited

U.S. PATENT DOCUMENTS

| | | | |
|---|---|---|---|
| 3,486,298 A | 12/1969 | Huebner | |
| 4,385,113 A * | 5/1983 | Frosch et al. | ...................... 435/8 |
| 5,024,762 A | 6/1991 | Ford | |
| 5,064,542 A | 11/1991 | Negersmith | |
| 5,200,065 A | 4/1993 | Sinclair | |
| 5,393,673 A * | 2/1995 | Gjerde et al. | ................. 436/171 |
| 5,769,539 A | 6/1998 | Tsang | |
| 5,947,689 A | 9/1999 | Schick | |
| 6,139,727 A | 10/2000 | Lockwood | |

(Continued)

FOREIGN PATENT DOCUMENTS

| | | |
|---|---|---|
| WO | WO2006096317 | 9/2006 |
| WO | WO 2006096317 A2 * | 9/2006 |

OTHER PUBLICATIONS

Hill, V. et al., "Multistate Evaluation of an Ultrafiltration-Based Procedure for Simultaneous Recovery of Enteric Microbes in 100-Liter Tap Water Samples", Appl Environ Microbiol., 2007 73(13):4218-4225.

(Continued)

*Primary Examiner* — Matthew O Savage
*Assistant Examiner* — Benjamin J Behrendt
(74) *Attorney, Agent, or Firm* — Pepper Hamilton LLP

(57) ABSTRACT

Methods of concentrating an analyte that is in liquid and method of detecting an analyte in a liquid are disclosed. Methods of screening a liquid for the presence of an analyte are also disclosed. Processes comprising continuously collecting a sample of fluid throughout the process and analyzing the sample are disclosed as are processes comprising treating ultrafilter membranes. Devices and systems for concentrating an analyte that is in liquid and for screening a liquid for an analyte are disclosed as well as devices and systems for concentrating an analyte from a continuous sample are disclosed.

28 Claims, 13 Drawing Sheets

(56) References Cited

U.S. PATENT DOCUMENTS

| | | |
|---|---|---|
| 6,174,437 B1 | 1/2001 | Haney |
| 6,192,168 B1 | 2/2001 | Feldstein |
| 6,306,350 B1 | 10/2001 | Mereish |
| 6,881,541 B2 * | 4/2005 | Petersen et al. ............ 435/6 |
| 6,949,355 B2 | 9/2005 | Yamanishi |
| 7,179,372 B2 | 2/2007 | Miller |
| 7,204,930 B2 | 4/2007 | Nightingale |
| 2001/0012612 A1 | 8/2001 | Petersen et al. |
| 2003/0052068 A1 * | 3/2003 | Lu ............................ 210/798 |
| 2004/0000515 A1 | 1/2004 | Harris |
| 2004/0241768 A1 | 12/2004 | Whitten et al. |
| 2007/0154492 A1 | 7/2007 | Michon et al. |
| 2008/0015361 A1 | 1/2008 | Khare et al. |

OTHER PUBLICATIONS

Hastie, J. C. et al., "Concentrating Giardia cysts in water by tangential flow filtration compared with centrifugation", New Zealand Journal of Marine and Freshwater Research, 1992, 26:275-278.

* cited by examiner

ANALYTE SCREENING AND DETECTION SYSTEMS AND METHODS

FIELD OF THE INVENTION

The present invention relates to systems and methods for concentrating and/or screening for and detecting the presence of analytes in large volumes of liquid.

BACKGROUND OF THE INVENTION

Numerous applications exist where it is desirable to screen for and detect the presence of small quantities of small sized particulates in large volumes of liquid. For example, detection of contaminants, disease markers, disease causing agents, or other small sized components which occur in small quantities in large volumes of liquid is desirable for the fields of health and safety, manufacturing, security and defense, and other areas in which the ability to detect the presence of minute sized particulates conveys an advantage or ability.

It is, for example, desirable to detect and quantify in foods and agricultural products analytes that may be indicative of the freshness or quality of the food, including beverages and water supplies. In routine quality control testing of foods, it is common practice to test for the presence of various contaminants, additives, degradation products, and chemical markers of microbial infestation, e.g., bacteria, bacterial endotoxins, mycotoxins, and the like. However, current methods by which such quality control testing is accomplished are typically either complex and skill-intensive analytical chemistry, molecular biology or biochemistry procedures or highly subjective and qualitative sensory evaluations, e.g., smell test, taste test, appearance, etc.

Likewise, the ability to detect contaminants in manufacturing processes, in safety and clean up processes, in the production, collection or isolation of medically useful materials, in public drinking water systems and reservoirs, waterways, bodies of water and tidal surf can provide a warning mechanism to prevent public health threats as well as the ability to identify the source and nature of such outbreaks. Moreover, protection against the dissemination of bioterrorism and chemical warfare agents, for example, is highly desirable to ensure public safety and protection.

Currently available systems have many shortcomings for meeting the challenges of detection of small particulates. For example, despite improvements in agriculture and food processing, outbreaks of disease from water-borne and food-borne pathogens still occur, including bacterial water- and food-borne diseases caused by *Clostridium botulinum* (botulism); *Clostridium perfringens* (food poisoning); *Staphylococcus aureus* (food poisoning); *Streptococcus* species (gastroenteritis); enteropathogenic *Escherichia coli* (gastroenteritis); *Shigella dysenteriae* (dysentery); *Salmonella* species (gastroenteritis); and *Vibrio cholerae* (cholera). There are also numerous water- and food-borne protozoan pathogens, such as *Entamoeba histolytica, Giardia lamblia, Cryptosporidium, Microsporidia*, and *Cyclospora*. In an attempt to avoid disease, food and water is often sampled and tested prior to distribution to determine whether it is contaminated by pathogenic microorganisms.

Numerous testing methods are available, but many common methods require that the number of organisms in a sample be expanded by promoting their reproduction prior to efforts to detect their presence. This pre-enrichment step which is performed on a specimen to increase the number of pathogenic organisms present is often time consuming; organisms are cultured in a non-selective growth medium typically for 24 hours or more. Pre-enrichment is usually necessary because pathogenic organisms may be present in very dilute amounts, thus making them difficult to detect in large volumes of liquid sample material. Second, an enrichment step may be performed in which a portion of the culture medium is transferred to an enrichment medium containing inhibitors that select for a pathogen of interest. The selected pathogen will grow further while other organisms are inhibited. Third, a measurement step is performed to discern whether pathogens of interest are present. Generally, a portion of the enrichment medium is streaked onto selective or differential agar media. The media will contain inhibitors effective against most organisms except the pathogen of interest. Indicator compounds (e.g. dyes) allow pathogen types to be visibly differentiated and thus indicate the presence and number of pathogens of interest. Exemplary alternative measurement steps are radioimmunoassay (RIA) tests, immunofluorescent assay (IFA) tests, enzyme immunoassay (EIA or ELISA) tests, DNA methods (e.g., PCR), and phage methods. For the food market, such methods are disadvantageous because they postpone distribution of fresh foodstuffs while specimens are culturing, particularly where freshness or spoilage concerns are present or it is otherwise impractical to store the food for extended periods. Furthermore, conventional methods typically only assay a small portion ($\leq 250$ g) of an agricultural crop, which may lead to analytical results that are not representative of a harvested crop as a whole. The small portion of the agricultural crop is randomly sampled across the crop population. For detecting a sporadic contamination event, this method has less than a 0.01% chance of finding the contamination.

A need exists for a convenient rapid, cost-effective, representative, and reliable method for testing for the presence of pathogens or infectious microorganisms, including during sporadic contamination events, in vegetables, fruits, nuts and other plant material intended, e.g., for animal or human consumption, and for devices and systems for carrying out such methods. A need exists for a convenient rapid, cost-effective, representative, and reliable method for concentrating an analyte which is present in small quantities in large volumes of liquid, including during sporadic contamination events, and for devices and systems for carrying out such methods.

SUMMARY OF THE INVENTION

The present invention relates to methods of concentrating an analyte that is in liquid. The methods comprise the steps of forming and collecting a retentate that contains an analyte. The retentate is formed by passing a liquid that contains an analyte through an ultrafilter membrane that the analyte cannot pass through using an ultrafilter membrane has a retentate side on which the liquid that contains the analyte is contacted and a permeate side from which a filtrate exits upon passing through the ultrafilter membrane. The retentate is collected by displacing filtrate from the permeate side of the ultrafilter membrane with a gas, flushing the retentate side of the ultrafilter membrane with gas and with liquid to produce a retentate solution that comprises the retentate, and collecting the retentate solution.

The present invention also relates to methods of detecting an analyte comprising concentrating an analyte that is in liquid and detecting analyte in the concentrating retentate solution.

The present invention further relates to methods of screening a liquid for the presence of an analyte. The methods comprise the steps of forming and collecting a retentate and screening the retentate for the presence of the analyte. The retentate is formed by passing a liquid that contains an analyte through an ultrafilter membrane that the analyte cannot pass through using an ultrafilter membrane has a retentate side on which the liquid that contains the analyte is contacted and a permeate side from which a filtrate exits upon passing through the ultrafilter membrane. The retentate is collected by displacing filtrate from the permeate side of the ultrafilter membrane with a gas, flushing the retentate side of the ultrafilter membrane with gas and with liquid to produce a retentate solution that comprises the retentate, and collecting the retentate solution. The retentate solution is then screened for presence of analyte.

The invention also provides processes that comprise the steps of performing one or more process cycles wherein each process cycle uses a quantity of fluid, wherein a fraction of the quantity of fluid is lost during the process cycle and a fraction of the quantity of fluid is recovered for reuse with new fluid in a subsequent process cycle; continuously collecting a sample of fluid throughout the process; wherein the sample is collected from the fraction of the quantity of fluid that is recovered for reuse; and analyzing the sample to determine whether an analyte is present in the sample.

The invention also provides processes comprising the steps of passing a first sample of liquid through an ultrafilter membrane; collecting retentate from the ultrafilter membrane; washing the ultrafilter membrane with an acidic solution; passing a second sample of liquid through an ultrafilter membrane; and collecting retentate from the ultrafilter membrane.

The present invention further relates to an apparatus for concentrating an analyte that is in liquid. The apparatus comprises an ultrafilter comprising an ultrafilter membrane that the analyte cannot pass through, wherein the ultrafilter membrane has a retentate side and a permeate side from which a filtrate exits upon passing through the ultrafilter membrane; two or more retentate access ports, wherein at least one retentate access port is connected by a valve and supply line to a source of liquid comprising an analyte to be concentrated, at least one retentate access port is connected by a valve and supply line to a source of a gas, at least one retentate access port is connected by a valve and supply line to a source of a rinsing liquid, and at least one retentate access port that is connected to valve and a collection line, wherein the retentate access port that is connected to valve and a collection line is not the same as the retentate access port that is connected by a valve and supply line to a source of a gas or the retentate access port that is connected by a valve and supply line to a source of a rinsing liquid, two or more permeate access ports; wherein at least one permeate access port is connected by a valve and drain line, and at least one permeate access port is connected by a valve and supply line to a source of a gas, wherein at least one permeate access port that is connected to valve and a drain line is not the same as the permeate access port connected by a valve and supply line to a source of a gas and a programmed computer operably linked to each valve and programmed to perform a process of concentrating an analyte in a liquid comprising the steps of forming a retentate that contains an analyte by contacting a liquid that contains the analyte with the retentate side of the ultrafilter membrane wherein filtrate passes through the membrane on the permeate side and the retentate that contains the analyte forms on the retentate side, and collecting the retentate by displacing filtrate from the permeate side of the ultrafilter membrane with a gas, and flushing the retentate side of the ultrafilter membrane with gas and with liquid to produce a retentate solution that comprises the retentate, and collecting the retentate solution.

The present invention further provides an apparatus for screening a liquid for an analyte.

The present invention further provides an apparatus for concentrating an analyte from a continuous sample. The apparatus comprises a first ultrafilter linked to a valve and supply line to a source of liquid comprising an analyte to be concentrated, a second ultrafilter linked to a valve and supply line to a source of liquid comprising an analyte to be concentrated, and a programmed computer operably linked to each valve and programmed to perform a process of concentrating analyte by opening the valve to the first ultrafilter linked to a valve and supply line to a source of liquid comprising an analyte to be concentrated and closing the valve to the second ultrafilter linked to a valve and supply line to a source of liquid comprising an analyte to be concentrated until initiation of collecting retentate from the first ultrafilter is to commence, whereby analyte is concentrated in the second ultrafilter by closing the valve to the first ultrafilter linked to a valve and supply line to a source of liquid comprising an analyte to be concentrated and opening the valve to the second ultrafilter linked to a valve and supply line to a source of liquid comprising an analyte to be concentrated.

DETAILED DESCRIPTION OF PREFERRED EMBODIMENTS

Figure 1:
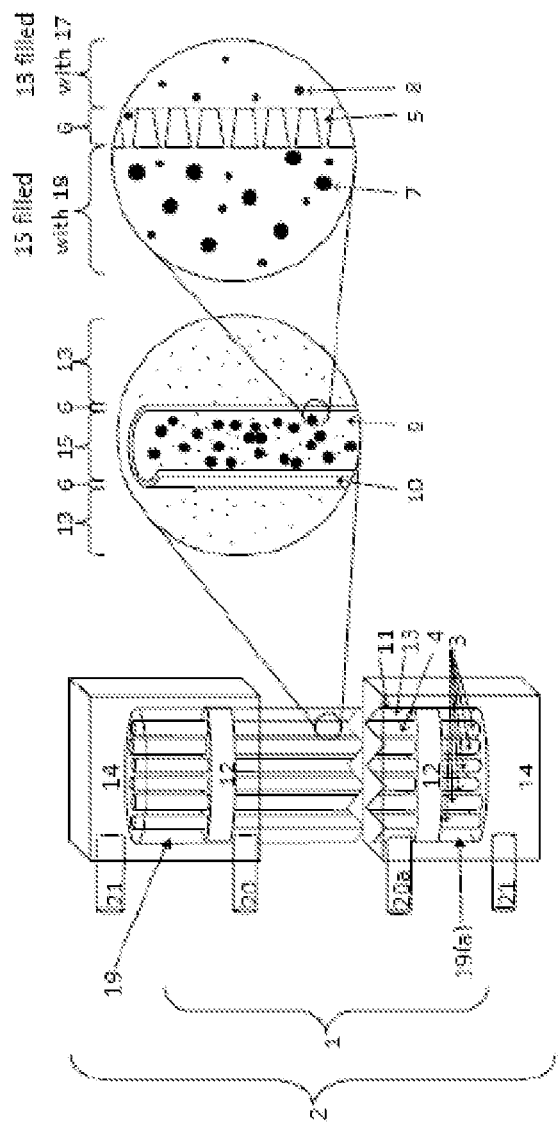
FIG. 1 depicts a typical ultrafilter assembly.
Figure 2:
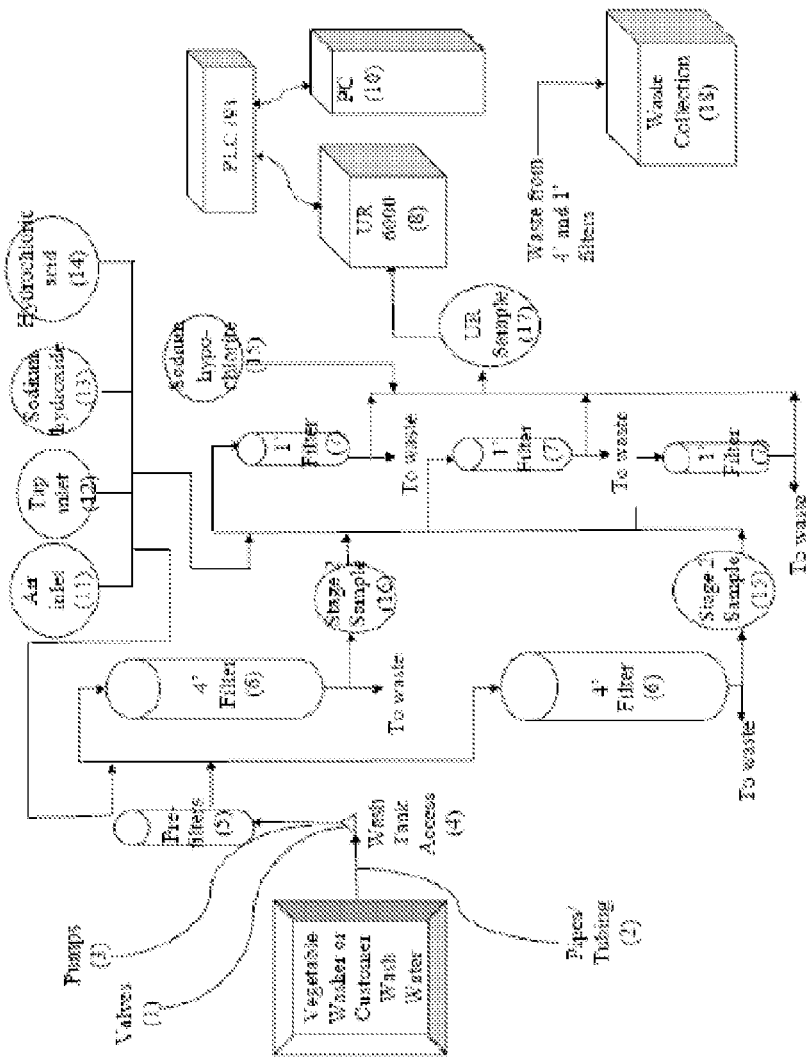
FIG. 2 depicts an embodiment of aspects of the invention which include parallel stage 1 and stage 2 filtration capabilities. The parallel stage 1 filters may be employed in an alternating fashion such that the use of the second stage 1 filter for filtration is initiated simultaneously with the initiation of collection of retentate solution from the first stage 1 filter and thereafter the filters alternate to provide continuous processing of continuously sampled material.
Figure 3:
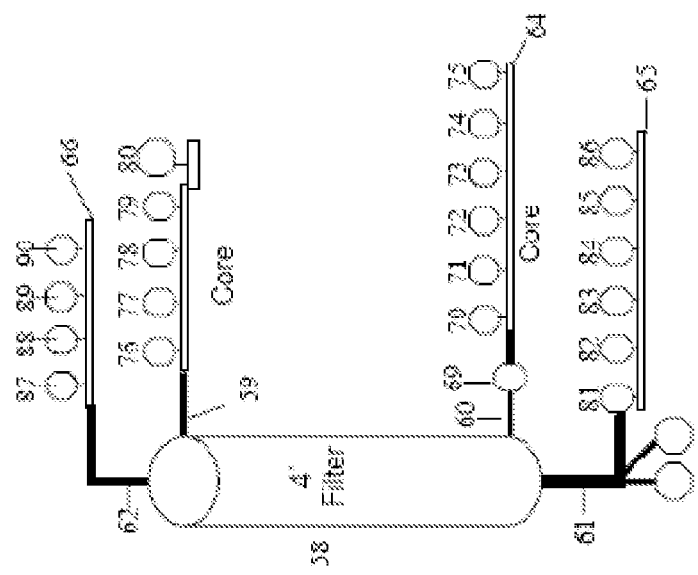
FIG. 3 depicts the stage 1 filter including valve assemblies described in Example 5.
Figure 4:
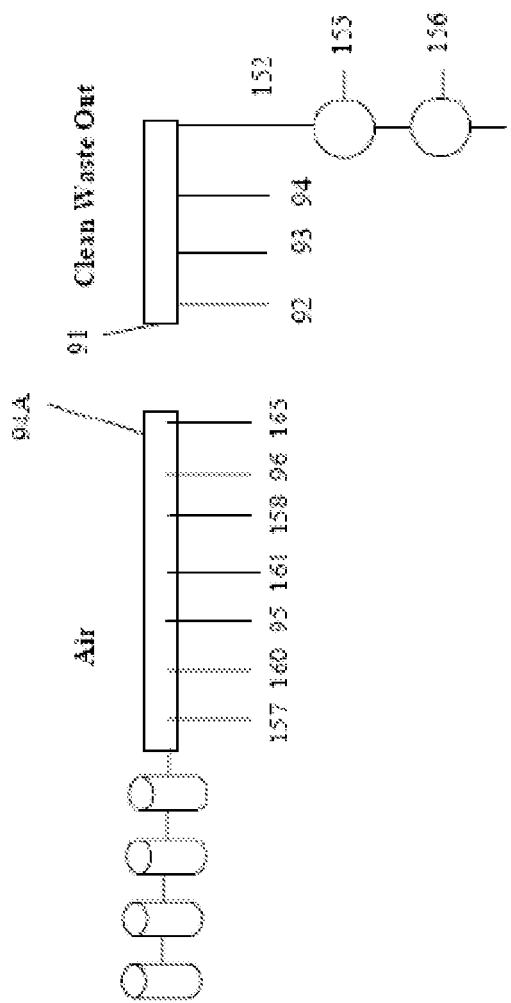
FIG. 4 depicts the air supply components including valve assemblies described in Example 5.
Figure 5:
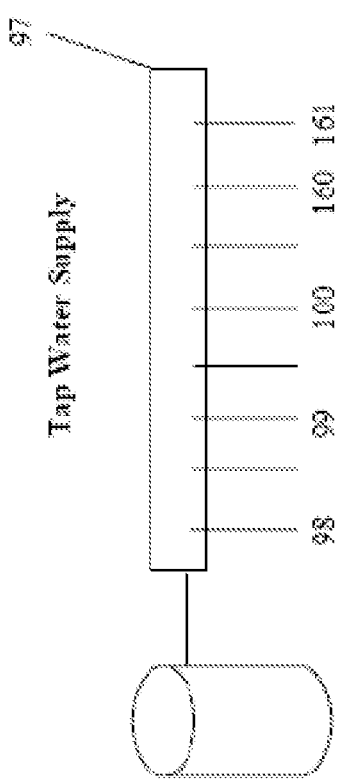
FIG. 5 depicts the tap water supply components including valve assemblies described in Example 5.
Figure 6:
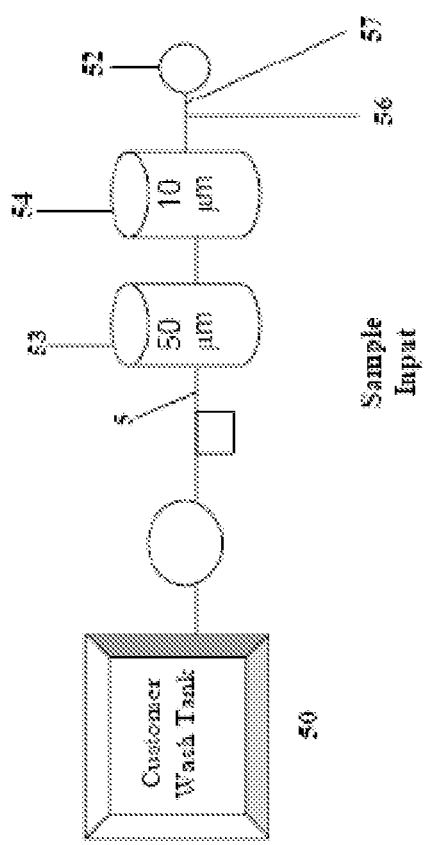
FIG. 6 depicts the wash water supply and pre-filter stage 1 assemblies described in Example 5.
Figure 7:
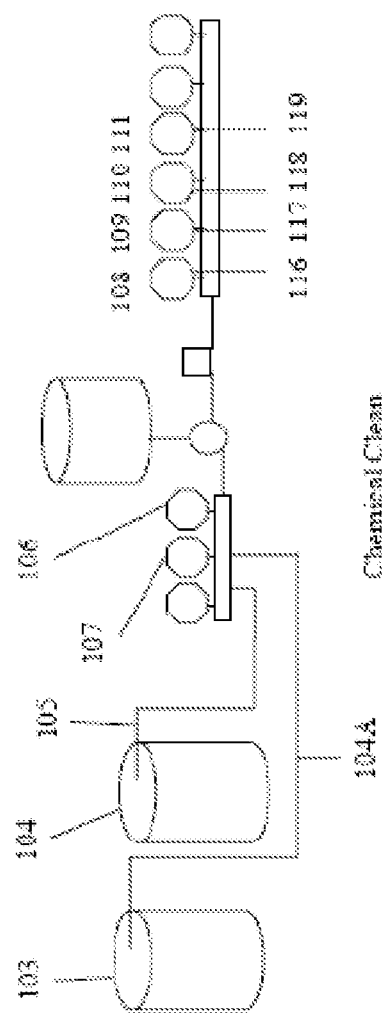
FIG. 7 depicts the chemical cleaning solution subsystem including valve assemblies described in Example 5.
Figure 8:
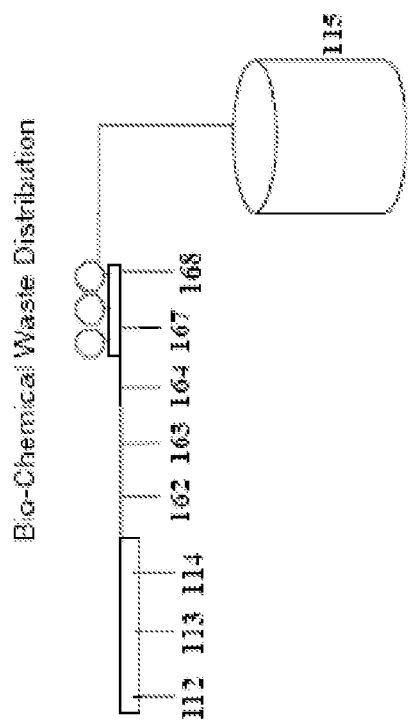
FIG. 8 depicts the chemical waste disposal assemblies described in Example 5.
Figure 9:
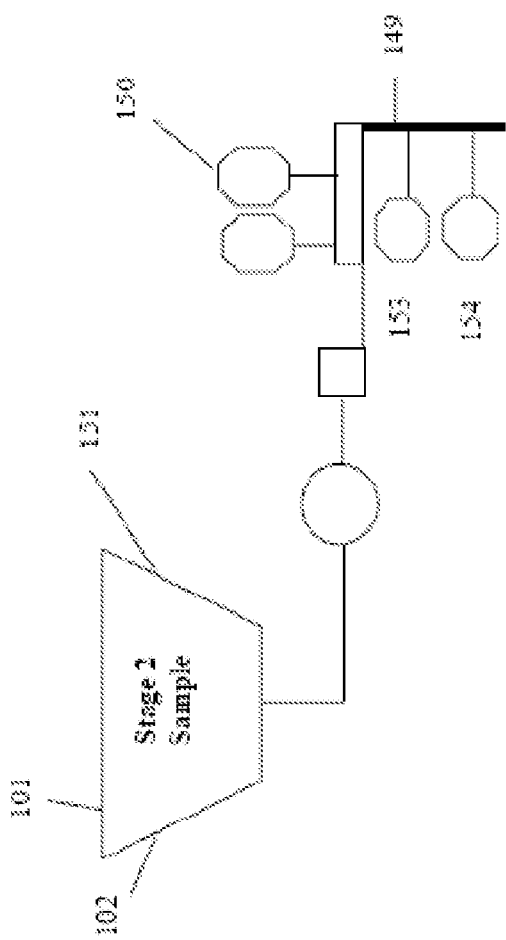
FIG. 9 depicts the stage 2 sample collection and distribution subsystem described in Example 5.
Figure 10:
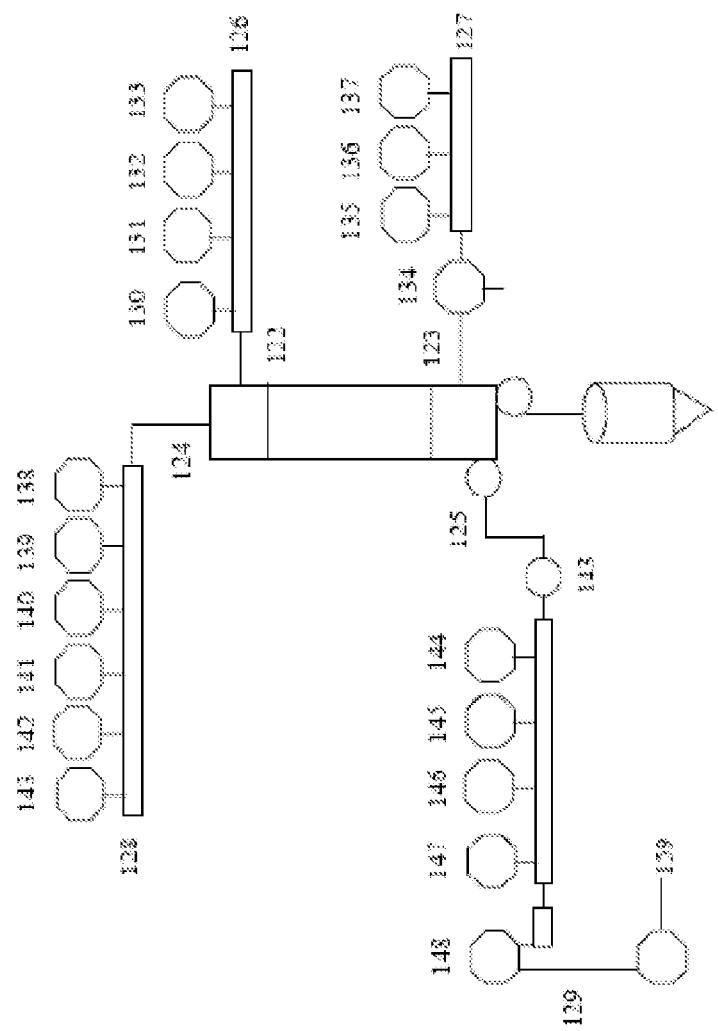
FIG. 10 depicts the stage 2 filter including valve assemblies described in Example 5.
Figure 11:
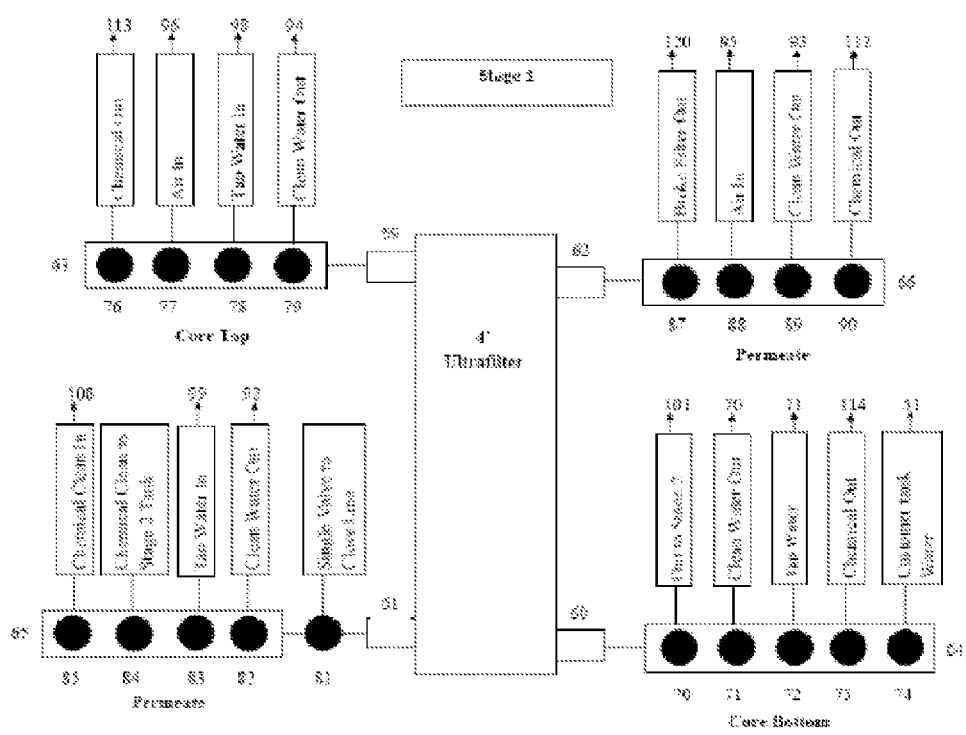
FIG. 11 depicts the stage 1 filter and valves described in Example 5.
Figure 12:
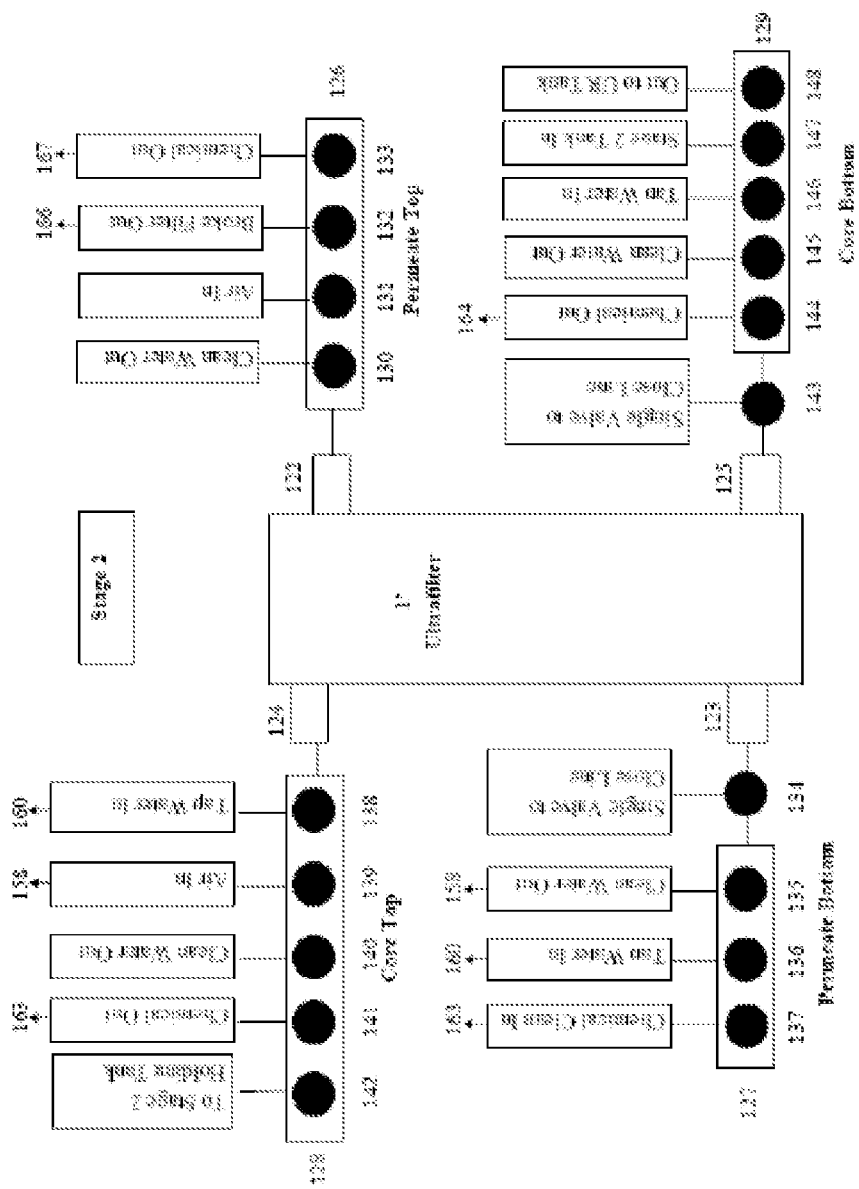
FIG. 12 depicts the stage 2 filter and valves described in Example 5.
Figure 13:
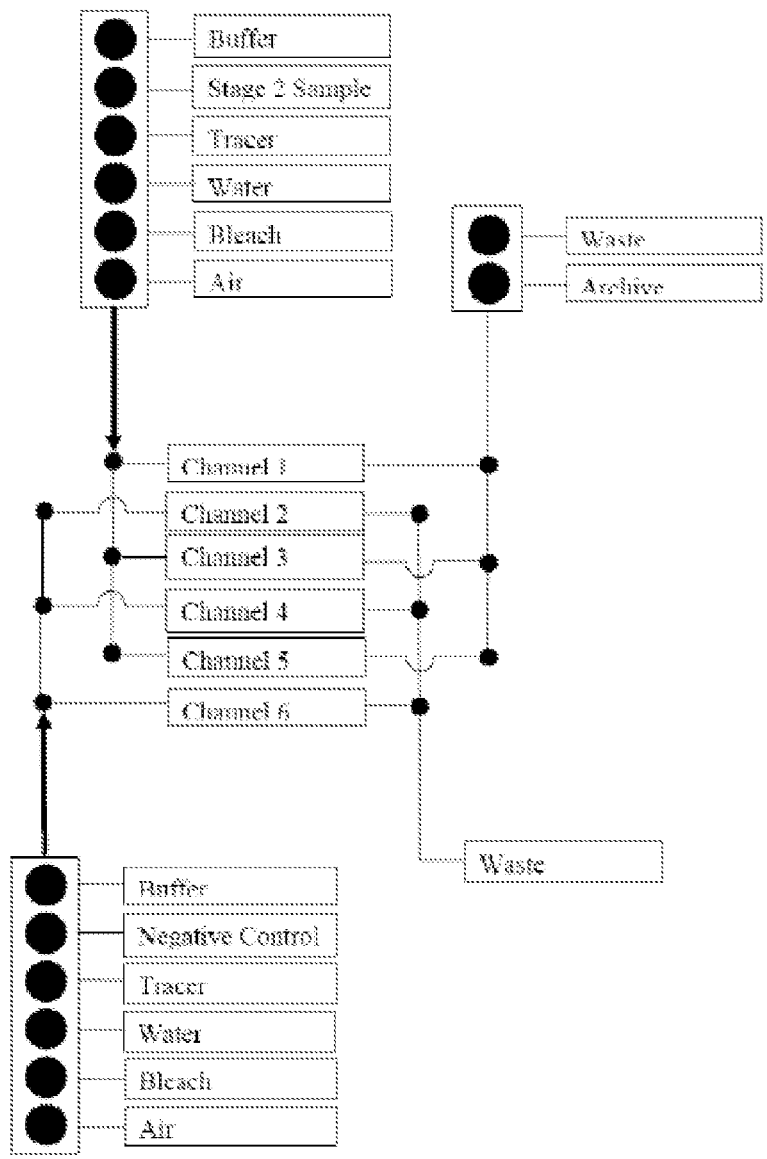
FIG. 13 depicts the fluid assembly for the array biosensor described in Example 5.

As used herein, the term "ultrafilter" is meant to refer to filters which have size cut-offs from 1 nm to 10000 nm. Accordingly, as used herein ultrafilters refer to filters which include nanofilters and those with smaller pore sizes as well as filters with larger than usual pore sizes. In some embodiments, filters have size cut-offs from 10 nm to 500 nm. In some embodiments, filters have size cut-offs from 20 nm to 100 nm. In some embodiments the size cut-off is about 10 nm. In some embodiments the size cut-off is about 20 nm. In some embodiments the size cut-off is about 30 nm. In some embodiments the size cut-off is about 40 nm. In some embodiments the size cut-off is about 50 nm. In some embodiments the size cut-off is about 60 nm. In some embodiments the size cut-off is about 70 nm. In some embodiments the size cut-off is about 80 nm. In some embodiments the size cut-off is about 90 nm. In some embodiments the size cut-off is about 100 nm. In some embodiments the size cut-off is about 200 nm. In some embodiments the size cut-off is about 300 nm. In some embodiments the size cut-off is about 400 nm. In some embodiments the size cut-off is about 500 nm. In some embodiments the size cut-off is about 600 nm. In some embodiments the size cut-off is about 700 nm. In some embodiments the size cut-off is about 800 nm. In some embodiments the size cut-off is about 900 nm. In some embodiments the size cut-off is about 1000 nm. In some embodiments the size cut-off is about 2000 nm. In some embodiments the size cut-off is about 3000 nm. In some embodiments the size cut-off is about 4000 nm. In some embodiments the size cut-off is about 5000 nm. In some embodiments the size cut-off is about 6000 nm. In some embodiments the size cut-off is about 7000 nm. In some embodiments the size cut-off is about 8000 nm. In some embodiments the size cut-off is about 9000 nm. In some embodiments the size cut-off is about 10000 nm or larger One aspect of the invention refers to improved methods of concentrating analytes which utilize ultrafilter membranes that comprise pores which are smaller than the size of the analyte to be concentrated. When passing a liquid containing the analyte through such a filter, the liquid passes through as a filtrate while the analyte cannot pass and forms a retentate. In some embodiments, systems and methods provide that liquid in the permeate space of the ultrafilter is displaced with gas and the ultrafilter core is flushed with a combination of liquid and gas to produce a highly concentrated retentate solution having a high yield of analyte. In some embodiments, the retentate solution is analyzed to detect analyte present. In some embodiments, the retentate solution is further concentrated prior to analysis. In some embodiments, the retentate solution is further concentrated prior to analysis using concentration technology as used in the formation of the retentate solution. In some embodiments, the retentate solution is further concentrated prior to analysis using different concentration technology.

FIG. 1 depicts a typical ultrafilter assembly 2 which is generally provided in the form of a cartridge 1 or module with end caps 14 at both ends. In some embodiments, the cartridge comprises a plurality of hollow, thin-walled, porous membrane tubes 3. The pore size, which defines the smallest opening of a pore 5 in the membrane wall 6 of an individual hollow, thin-walled, porous membrane tube 15 defines the size exclusion of the membrane. Particulates 7 larger than the pore size cannot pass through or permeate the membrane 6 whereas particulates 8 smaller than the pore size 5 can pass through. The inside surface 9 of a hollow, thin-walled, porous membrane tube 4 is referred to as the retentate side and forms the core 15 of the tube 4. The outer surface 10 of a hollow, thin-walled, porous membrane tube 15 is referred to as the outside or permeate side of the tube 4. Typically, the bundle of membrane tubes 3 is contained in a cylindrical housing 11. At each end of the bundle is an impermeable barrier 12 through which each of the individual tubes 4 of the bundle 3 extends. The space within the housing 11 and between the each of the two barriers 12 around the outside surfaces 10 of each tube 4 of the bundle of tubes 3 is referred to as the permeate space 13.

Typically at each end are caps, covers or housing members 14 over the barriers 12 which allow flow to enter the core 15 of each membrane tube 4 which form a retentate space 19 and 19a between the barrier 12 and the end cap 14. Liquid 18 entering the retentate space 19 through flow port 20 can flow through the cores 15 and into the other retentate space 19a. To enter into the permeate space 13, the liquid 18 must travel through the pores 5 of the membranes 4. Liquid that passes though the membrane 4 and enters the permeate space 11 is referred to permeate or filtrate 17. Material retained in the core 15 is referred to as retentate. Particulates 7 larger than the size of the pores 5 that cannot pass through or permeate the membrane 4 thus form the retentate while particulates 7 smaller than the size of the pores 5 can pass through the membrane 4 with the liquid and form the filtrate 17.

In systems and methods of concentrating an analyte the pore size is selected to be sufficiently small to prevent passage of the analyte through the membrane. Thus, the analyte becomes concentrated in the retentate. Recovery of the retentate in high yield and high concentration is desirable as it is important to recover as much analyte as has been collected in the retentate. It is important to do so while minimizing the dilution of the analyte in the recovery process so that the detection technology employed can operate with as concentrated a sample as possible. Accordingly, systems and methods which can recover high yield at high concentrations are desirable and necessary to improve the ability to detect analyte.

Referring to FIG. 1, the high yield recovery of analyte in retentate at high concentrations may be achieved by displacing filtrate 17 from the permeate space 11 with a gas and rinsing the cores 15 and retentate space 19 and 19a with a combination of gas and liquid. A high proportion of analyte in retentate (high yield) may be recovered in minimal volumes of liquid (high concentration) using this combination of conditions and techniques. During the ultrafiltration step, liquid to be filtered enters the ultrafilter cartridge 1 by entering the retentate space 19 and 19a through either one or both of retentate access ports 20 and 20a. If liquid enters the ultrafilter through a single retentate access port 20 or 20a, the other of the two retentate access ports 20 and 20a is closed. Liquid enters the cores 15 of the membrane tubes 4 and passes through the pores 5 of the membrane 6, whereupon it enters the permeate space 13. The liquid in the permeate space 13 is filtrate 17. The filtrate 17 exits the permeate space 13 through either one or both of permeate access ports 21 and 21a. If filtrate 17 exits the permeate space 13 through a single permeate access port 21 or 21a, the other of the two permeate access ports 21 and 21a is closed. During the retentate collection step, the flow of liquid into the retentate space 19 and 19a through one or both of retentate access ports 20 and 20a is discontinued. Filtrate is removed from the permeate space 13 by introducing a gas into the permeate space 13 through one of the permeate access ports 21 or 21a whereby the filtrate 17 exits the permeate space 13 through the other of the two permeate access ports 21 or 21a. The retentate 18 is removed from the cores 15 of the membranes tubes 4 and from the retentate space 19 and 19a by introducing a gas and a quantity of liquid into one of the two retentate spaces 19 and 19a through one of retentate access port 20 or 20a whereby the retentate 18 exits the cores and retentate spaces 19 and 19a through the other of retentate access port 20 or 20a. The collected liquid, which includes the retentate 18, may be analyzed for the presence of one or more analytes or further concentrated prior to analysis.

The analyte concentration and recovery conditions and techniques are particularly useful when used in multistage concentration systems and methods. In some embodiments, analyte is concentrated from original sample material using a two stage system in which each stage is an ultrafiltration concentration in which the retentate is recovered in high yield and at high concentrations that may be achieved by displacing filtrate from the permeate space with a gas and rinsing the cores and retentate space with a combination of gas and liquid. In some embodiments, analyte is concentrated from original sample material using a two stage system in which the first stage is an ultrafiltration concentration in which the retentate is recovered in high yield and at high concentrations that may be achieved by displacing filtrate from the permeate space with a gas and rinsing the cores and retentate space with a combination of gas and liquid and second stage is a different concentration technology such as those using magnetic beads, those using other types of ultrafilters and/or those using dielectrophoresis. In some embodiments, analyte is concentrated from original sample material using a two stage system in which the second stage is an ultrafiltration concentration in which the retentate is recovered in high yield and at high concentrations that may be achieved by displacing filtrate from the permeate space with a gas and rinsing the cores and retentate space with a combination of gas and liquid using material concentrated in the first stage using different concentration technology such as those using magnetic beads, those using other types of ultrafilters and/or those using dielectrophoresis. In some embodiments, three, four, and five stage systems may be employed using all stages in which concentration is achieved by ultrafiltration concentration in which the retentate is recovered in high yield and at high concentrations may be achieved by displacing filtrate from the permeate space with a gas and rinsing the cores and retentate space with a combination of gas and liquid. In some embodiments, three, four, and five stage systems may be employed using one, two, three, or four stages in which concentration is achieved by ultrafiltration concentration in which the retentate is recovered in high yield and at high concentrations that may be achieved by displacing filtrate from the permeate space with a gas and rinsing the cores and retentate space with a combination of gas and liquid and other stages being one or more of the same or different technologies such as for example those using magnetic beads, those using other types of ultrafilters and/or those using dielectrophoresis.

Some embodiments refer to systems and methods of preparing a retentate solution. In some embodiments, systems and methods are provided to concentrate an analyte that is known to be present in a liquid. In some embodiments, systems and methods are provided to detect an analyte that is known to be present in a liquid. In some embodiments, systems and methods are provided to screen a liquid to determine whether or not there is any analyte present in the liquid.

Examples of filters that may be used include, but are not limited, to ultrafilters, nanofilters, any hollow fiber filter, flat filters, and membrane filters.

In some embodiments, sample liquid is pre-filtered prior to concentration. Examples of filters that may be used include, but are not limited to, plastic mesh, metallic mesh, plastic screens, metallic screens, bed filters, media-type filters, bag filters, and flat filters.

Examples of the fittings that may be used include, but are not limited to, plastic, stainless steel, copper, brass, and Teflon® coated.

Examples of pumps that may be used include, but are not limited to, syringe pumps, double diaphragm pumps, single diaphragm pumps, solenoid pumps, gear pumps, and centrifugal pumps.

Examples of valves that may be used include, but are not limited to, solenoid valves, ball valves, air-operated valves, elliptic valves, diaphragm valves, metering valves, needle valves, butterfly valves, and check valves.

Examples of gases used to displace liquid in the permeate space, include, but are not limited to, compressed air, nitrogen, argon, oxygen, hydrogen, helium, and xenon. Gas pressures used should not to exceed the pressure which will damage the membrane. In some embodiments, compressed air is used at a pressure between about 1 psi to 80 psi. In some embodiments, compressed air is used at a pressure between 25 psi to 45 psi. In some embodiments, an atmospheric drain is used. In some embodiments, compressed air is used to displace liquid in the permeate space for about 1 second to 30 seconds or more.

Examples of gases used to rinse the cores, include, but are not limited to, compressed air, nitrogen, argon, oxygen, hydrogen, helium, and xenon. Gas pressures used should not to exceed the pressure which will damage the membrane. In some embodiments, compressed air is used at a pressure between about 1 psi to 80 psi. In some embodiments, compressed air is used at a pressure between 20 psi to 45 psi. In some embodiments, an atmospheric drain is used. In some embodiments, compressed air is used to rinse the core for about 1 second to 30 seconds or more.

In some embodiments, air pressure for outside of a 4' stage 1 ultrafilter ranges from gravity drain to 80 psi. In some embodiments, 5 psi, 10 psi, 15 psi, 20 psi, 25 psi, 30 psi, 35 psi, 40 psi, 45 psi, 50 psi, 55 psi, 60 psi, 65 psi, 70 psi, 75 psi or 80 psi are used. In some embodiments, air pressure for outside of a 4' stage 1 ultrafilter ranges from gravity drain to 80 psi. In some embodiments, 5 psi, 10 psi, 15 psi, 20 psi, 25 psi, 30 psi, 35 psi, 40 psi, 45 psi, 50 psi, 55 psi, 60 psi, 65 psi, 70 psi, 75 psi or 80 psi. Air pressure for outside of 1' stage 2 ultrafilter ranges from gravity drain to 80 psi. In some embodiments, 5 psi, 10 psi, 15 psi, 20 psi, 25 psi, 30 psi, 35 psi, 40 psi, 45 psi, 50 psi, 55 psi, 60 psi, 65 psi, 70 psi, 75 psi or 80 psi are used. Air pressure for core of 1' stage 2 ultrafilter range from gravity drain to 80 psi. In some embodiments, 5 psi, 10 psi, 15 psi, 20 psi, 25 psi, 30 psi, 35 psi, 40 psi, 45 psi, 50 psi, 55 psi, 60 psi, 65 psi, 70 psi, 75 psi or 80 psi are used.

Examples of liquids used to rinse the cores include, but are not limited to, tap water, sample water, filtrate, distilled water, aqueous surfactant solution, acid solutions such as acetic acid, acidified bisulfite, ascorbic acid, citric acid, hydrochloric acid, nitric acid, oxalic acid, and sulfuric acid, basic solutions such as lithium hydroxide, potassium hydroxide, and sodium hydroxide, and other sanitizing or cleaning chemicals such as sodium hypochlorite, urea, and ethylenediaminetetraacetic acid (EDTA). In some embodiments, 5 ml to several gallons of tap water is added. In some embodiments, tap water is added for 1 second to 15 minutes. In some embodiments, bases such as sodium hydroxide and acids such as hydrochloric acid may be used at various concentration ranging from 0.1% to very concentrated solutions. In some embodiments, the sodium hydroxide and hydrochloric acid percentage are each used independently from 0.5 to 10%. In some embodiments, from 1-5%. In some embodiments, about 1%, about 2%, about 3%, about 4%, or about 5%. Time exposure to ultrafilter by sodium hydroxide and hydrochloric acid ranges from several minutes to overnight. In some embodiments, 2 minutes to 2 hours. In some embodiments 5 minutes to 30 minutes. In some embodiments, 10-15 minutes, One to ten cycles may be used. In some embodiments, 1, 2, 3, 4, 5, 6, 7, 8 or 9 cycles are performed independently for each cleaning solution. In some embodiments, 3 liters or 30 liters of cleaning solution used. In some embodiments, 3, 4, 5, 6, 7, 8, 9, 10, 15, 20, 25 or 30 liters of cleaning solution used. In some embodiments, 1 liters or 10 liters of cleaning solution used. In some embodiments, 0.5, 1, 2, 3, 4, 5, 6, 7, 8 or 9, liters of cleaning solution used. Sanitizing solutions, such as Sodium hypochlorite, may be used at various concentration ranging from 0.1% to about 6%. In some embodiments, 0.2 to 4%. In some embodiments, about 0.4, about 0.6 about 0.8, about 1.0, about 1.2, about 1.4, or about 1.6% are used. Sodium hypochlorite may be used to clean biosensor, in some embodiments 5-250 ml. for the UltraRapid 6000. In some embodiments, 10 ml, 20 ml, 30 ml, 40 ml, 50 ml, 60 ml, 70 ml, 80 ml, 90 ml, or 100 ml are used. In some embodiments, filtered tap water used for rinsing stage 2 filter may range from 0-200 ml. In some embodiments, 10 ml, 20 ml, 30 ml, 40 ml, 50 ml, 60 ml, 70 ml, 80 ml, 90 ml, 100 ml, 150 ml, or 200 ml are used. In some embodiments, filtered tap water pressure 2-60 psi. In some embodiments, 5 psi, 10 psi, 15 psi, 20 psi, 25 psi, 30 psi, 35 psi, 40 psi, 45 psi, 50 psi, 55 psi, or 60 psi is used. In some embodiments, filtered tap water pressure flow rate is 1-20 gallons/minute or full flow at 60 psi. In some embodiments, it is 1-2 gallons/minute, 1-4 gallons/minute, 1-6 gallons/minute, 1-8 gallons/minute, 1-10 gallons/minute, 1-12 gallons/minute, 1-14 gallons/minute, 1-16 gallons/minute or 1-18 gallons/minute.

Systems and methods for concentration of analytes at high yield and high concentration are particularly useful when performed as part or systems and methods of screening for or detecting analytes. Examples of detection technologies include, but are not limited to, biosensors, ELISA, PCR, GLISA, selective media, lateral flow, immunomagnetic separation, electrochemiluminescence, chromogenic media, immunodiffusion, DNA hybridization, staining, colorimetric detection, ionic pathways in living organisms, other living organism indicators, luminescence and detection of biomarkers such as antibodies, phage, DNA and aptamer. In some embodiments, array biosensors are used to analyze concentrated samples of the presence of analytes. UltraRapid 2020 (UR-2020), UltraRapid 5000 (UR-5000), UltraRapid 6000 (UR-6000) (Hanson Technologies, Carlisle, Pa.) or a biosensor array as disclosed in U.S. Pat. No. 6,192,168, which is incorporated herein by reference, may be used to analyze concentrated samples of the presence of analytes. Other biosensors that could be used include, but are not limited to, Biocontrol Assurance GDS, Dupont BAX, Warnex Rapid Pathogen, Merck Singlepath GLISA pathogen test, and Neogen Reveal. Anti-*E. coli* O157:H7 antibodies include Catalog Nos: E3500-27, E3500-25, E3500-28, E3500-26A, E3500-24, E3500-06, E3500-21, E3500-07, E3500-23, E3500-08, E3500-09, E3500-06A, E3500-24A, E3500-06C, E3500-06D, E3500-06J, E3500-06K, E3500-06M (United States Biological, Swampscott, Mass. (MA) 01907); Catalog Nos.: G5V119-500 and MAV 119-499 (Meridian Life Science, Inc. Cincinnati, Ohio; Catalog No.: MAB772P (Maine Biotechnology Services, Inc. Portland Me.) and Catalog No.: 01-95-90 (KPL, Inc. Gaithersburg, Md.).

Analytes which can be detected include, but are not limited to, various compounds such as biological and chemical agents such as bacteria, allergens, fungi, viruses, mycoplasms, protozoans, algae, parasites, prions, toxins, pesticides, nucleic acids, proteins and peptides. Examples of some analytes of interest are listed in the Table I below. Typically, miocroorganisms (including single cell prokaryotic and eukaryotic organisms, viruses, prions, larvae, eggs and other life stages of parasitic organisms) are detected using detection of one or more proteins of the microorganism.

Examples of applications and industries where the systems and methods may be used include screening food products for contaminants such as screening produce, meat, seafood, processed foods and beverages (alcoholic and non-alcoholic). In some embodiments, used cleaning solutions may be concentrated using systems and methods to confirm that contaminants have been removed or are otherwise not present. Municipal water supplies can similarly be screened for contaminants. Similarly, waterways and bodies of water such as rivers, creeks, streams, lakes, canals, can be screened to assay for water quality. Ocean monitoring may also be performed, particularly surf and other bathing areas. Oceans, waterways and bodies of water may be screened for manufacturing waste and other pollutants. In addition to contaminant detection, the systems and methods may be used to concentrate small quantities of materials produced or contained in large volumes of liquid such as manufacturing process, purification and isolation processes. Similarly, systems and methods may be used in medical diagnostics, and blood and other fluid screening, and tissue and organ screening.

In some embodiments, a single cleaning cycle is employed between concentration/recovery cycles. In some embodiments, multiple cleaning cycles are employed between concentration/recovery cycles. In some embodiments, multiple different cleaning cycles are employed between concentration/recovery cycles. In some embodiments, one or more cleaning cycles are employed in which one or more cleaning cycles comprise back-flushing with a basic solution. In some embodiments, one or more cleaning cycles are employed in which one or more cleaning cycles comprise forward flushing/rinsing with a basic solution. In some embodiments, one or more cleaning cycles are employed in which one or more cleaning cycles comprise back-flushing with an acid solution. In some embodiments, one or more cleaning cycles are employed in which one or more cleaning cycles comprise forward flushing/rinsing with an acid solution. In some embodiments, one or more cleaning cycles are employed in which one or more cleaning cycles comprise back-flushing with a sanitizing solution. In some embodiments, one or more cleaning cycles are employed in which one or more cleaning cycles comprise forward flushing/rinsing with a sanitizing solution Examples of cleaning cycles comprising an acidic solution may include the steps of back-flushing the filter with an acid solution so that the acidic solution is present on both the core and permeate sides of the membrane where after the filter is maintained for a period of time to allow cleaning such as several minutes to overnight, in some embodiments 5-30 minutes and in some embodiments, 10-15 minutes. Following acid soak, the acid solution is removed and, in some embodiments, the filter is back-flushed with a neutral solution. Examples of cleaning cycles comprising a basic solution may include the steps of back-flushing the filter with a basic solution so that the basic solution is present on both the core and permeate sides of the membrane where-after the filter is maintained for a period of time to allow cleaning such as several minutes to overnight, in some embodiments 5-30 minutes and in some embodiments, 10-15 minutes. Following base soak, the basic solution is removed and in some embodiments, the filter is back-flushed with a neutral solution.

In some embodiments, the basic cleaning cycle occurs first, followed by the neutral cleaning cycle, followed by the acid cleaning cycle, followed by a neutral cleaning cycle. In some embodiments, the acid cleaning cycle occurs first, followed by the neutral cleaning cycle, followed by the basic cleaning cycle, followed by a neutral cleaning cycle. In some embodiments, a cleaning cycle using a sanitizing agent is employed. Examples of acidic cleaning solutions include but are not limited to, acetic acid, acidified bisulfite, ascorbic acid, citric acid, hydrochloric acid, nitric acid, oxalic acid, and sulfuric acid. Preferred pH is in the range of 0-6. Examples of basic cleaning solutions include but are not limited to lithium hydroxide, potassium hydroxide, and sodium hydroxide. Preferred pH is in the range of 8-14. Examples of other chemicals that can be used as sanitizing agents include, but are not limited to, sodium hypochlorite, urea, and ethylenediaminetetraacetic acid (EDTA).

Another aspect of the invention relates to methods of concentrating analytes by ultrafiltration, wherein the ultrafilter membrane undergoes one or more cleaning cycles comprising contacting the membrane with an acidic solution. This aspect of the invention may be particularly useful in systems and processes in which ultrafilters are used in repeated filtration steps whereby they are cleaned prior to each reuse. It is particularly useful to employ acid wash cleaning when filtering materials that cause mineral deposition in the filter membrane. According to this aspect of the invention, cleaning steps between each use of the ultrafilter for filtration of a liquid comprises the step of cleaning the ultrafilter with an acid solution. Some embodiments of this aspect of the invention employ the method of first displacing liquid in the permeate side with air and then rinsing the core with air and/or liquid, then cleaning the core with an acid. Some embodiments of this aspect of the invention employ the method clearing the core by an air blow and/or liquid forward flush. Some embodiments of this aspect of the invention employ the method clearing the core by back-flush, and then cleaning the core with an acid. In some embodiments, the acid cleaning step comprises back-flushing the filter with an acid solution. In some embodiments, the acid cleaning step comprises forward-flushing the filter with an acid solution. In some embodiments, the ultrafilter membrane undergoes one or more cleaning cycles comprising an acidic solution in combination with one or more cleaning cycles comprising a basic solution. In some embodiments, the cleaning cycles comprising an acidic solution precede the cleaning cycles comprising a basic solution. In some embodiments, the cleaning cycles comprising basic solution precede with cleaning cycles comprising acidic solution. In some embodiments, one or more cleaning cycles comprising a neutral solution precede and/or follow the cleaning cycles comprising an acidic solution. In some embodiments, one or more cleaning cycles comprising a neutral solution precede and/or follow the cleaning cycles comprising a basic solution.

Examples of cleaning cycles comprising contacting the membrane with an acidic solution include the steps of back-flushing and/or forward flushing the filter with an acid solution so that the acidic solution is present on both the core and permeate sides of the membrane where after the filter is maintained for a period of time to allow cleaning such as several minutes to overnight, in some embodiments 5-30 minutes and in some embodiments, 10-15 minutes. Following acid soak, the acid solution is removed and in some embodiments, the filter is back-flushed and/or forward flushed with a neutral solution. In some embodiments, in addition to cleaning with an acid solution, the membrane is contacted with a basic solution. Examples of cleaning cycles comprising contacting the membrane with a basic solution include the steps of back-flushing and/or forward flushing the filter with a basic solution so that the basic solution is present on both the core and permeate sides of the membrane where-after the filter is maintained for a period of time to allow cleaning such as several minutes to overnight, in some embodiments 5-30 minutes and in some embodiments, 10-15 minutes. Following the base soak, the basic solution is removed and in some embodiments, the filter is back-flushed and/or forward flushed with a neutral solution. In some embodiments, the basic cleaning cycle occurs first, followed by the neutral cleaning cycle, followed by the acid cleaning cycle, followed by a neutral cleaning cycle.

Examples of acidic cleaning solutions include, but are not limited to, acetic acid, acidified bisulfite, ascorbic acid, citric acid, hydrochloric acid, nitric acid, oxalic acid, and sulfuric acid. Preferred pH is in the range of 0-6. Examples of basic cleaning solutions include but are not limited to lithium hydroxide, potassium hydroxide, and sodium hydroxide. Preferred pH is in the range of 8-14.

In some embodiments, additional cleaning cycles are performed using one or more sanitizing solutions. Examples of sanitizing solutions include, but are not limited to, sodium hypochlorite, urea, and ethylenediaminetetraacetic acid (EDTA).

Another aspect of the present invention relates to systems and methods for continuous sampling of processes which use a fluid such as a gas or liquid. This aspect of the invention may be particularly useful in systems and processes in which it is not practical or possible to sample complete batches of fluid in process or in processes in which fluids are continuously transporting through a system.

Continuous sampling refers to the process of removing a sample for testing/monitoring over a period of continuous production as distinguished from batch sampling in which a sample is removed for testing at a specific time point. Continuous sampling allows for more effective monitoring in systems and processes in which a continuous process employing multiple process cycles are performed during which there is a loss of fluid, a recovery of used fluid for reuse and a replacement of lost fluid in each subsequent process cycles. In such systems and processed, the presence of a sporadic contaminant can be more difficult to detect using batch sampling because the continuous process results in a continual dilution of the recovered fluid by replacement fluid. Continuous sampling allows for more efficient monitoring by eliminating the need to sample each batch separately. Each batch of a multi-batch process provides a specific quantity of sample material in each sample tested. There is a greater difficulty in detecting a sporadic contaminant or other random appearance of an analyte when sampling a single batch in a multi-batch process. Continuous sampling provides a higher degree of detecting the sporadic contaminant or other random appearance of an analyte.

In some embodiments, a multi-batch process comprises at least two process cycles, at least three process cycles, at least four process cycles, at least five process cycles, at least six process cycles, at least seven process cycles, at least eight process cycles, at least nine process cycles, or at least ten process cycles. In some embodiments, a multi-batch process comprises eleven or more process cycles, fifteen or more process cycles, twenty or more process cycles, thirty or more process cycles, or forty or more process cycles.

Continuous processes include numerous processes which may or may not reuse fluids and replace lost fluids during the process. Continuous processes include continuous process washing procedures. Continuous process produce washing is an example of a continuous process washing procedure. In a typical continuous process produce washing procedure, a process cycle includes contacting solid objects, such as fruits, vegetables, berries, tubers or roots, with a washing liquid, typically water, and the wash liquid is recovered for reuse. Some washing liquid, however, is lost due to spillage, adherence to the washed produce, absorption and/or evaporation. In the next process cycle, the recovered wash liquid is used together with additional washing liquid that is provided to replace the lost washing liquid and the liquid is again recovered for reuse. To detect the presence of contaminants on any of the produce washed in the process cycle, a sample of the recovered liquid must be taken for each process cycle. Following a singular introduction of a contaminant that occurs when contaminated produce is washed, recovered liquid from a subsequent process cycle will have decreasing amounts of contaminants because of the loss of liquid and its replacement with new liquid. Thus, monitoring must occur throughout the process. Continuous sampling provides an efficient method of monitoring such continuous process.

Another example of continuous processing for which continuous sampling is well suited is in the collection or manufacture of fluid beverages and food products. It is typical in many such processes that collected or manufactured fluids are transported through piping to storage or dispensing tanks form which the deposited fluid is distributed. In such systems there is a mixing of fluids collected produced at different times and/or from different sources. As a storage or dispensing tank is being filled, it is also being emptied. When a contaminant is introduced, the quantity of contaminant is at a peak and over time the quantity reduces as the tank is emptied and refilled. Continuous sampling allows for an efficient method of monitoring the fluids collected or manufactured in these processes.

Continuous sampling provides improved efficiency in monitoring in applications in which fluids produced or used in the processes are not contained in isolated batches and there is a risk of a random contamination or occurrence of an analyte in the fluid.

Continuous sampling is also useful in processes involving the continuous flow of fluids through a system. Any fluid that passes through a conduit can be the subject of continuous sampling. A sample is collected by continuously removing a quantity of the fluid that is flowing in the conduit and the sample is then tested while another sample is collected.

In some embodiments, systems and methods which employ continuous sampling comprise two or more collection components which maintained in parallel to each other and used alternatively. For example, in systems and methods using a concentrator comprising a filter, the sample collection flow can be routed to a first filter, and upon initiation of the retentate recovery, the sample collection flow can be routed to a second filter while the first filter undergoes collection, then cleaning cycles, and so forth. Thus, the sample collection continues as long as the process or fluid flow continues. In some embodiments, a single sample processing apparatus is used. The sample follows continuously to collection tank and is removed for monitoring at a rate comparable to its collection. In some embodiments, the sample follows continuously to monitoring equipment which immediately processes the sample for detection.

The invention is further illustrated by the following examples, which should not be construed as further limiting.

EXAMPLES

Example 1

Valves, tubes and pumps form connections between a wash tank access fitting, filters, and an air port. Valves and pumps are controlled by computer using a computer program. The computer program interface uses a National Instruments Lab-Windows platform as the base graphical user interface.

For a produce screening application, wash water samples are supplied to an OmniFresh 1000™ Vegetable Wash Screening System from a vegetable wash tank. Wash water from the wash tank (the raw sample) is introduced into the system by pumping it through a set of pre-filters to remove large particulates. The pre-filtered sample (pre-filtered raw sample) is pumped through valves and tubing leading to a first stage ultrafilter which is a 4' ultrafilter, X-Flow model type S-30 FSFC PSU. The membrane diameter is 0.8 mm, the membrane area is 6.2 $m^2$, the length is 1047 mm, and the pore is 25-35 nm Sample wash water is continuously pumped through the pre-filter and ultrafilter at a constant rate while the entire lot of produce is being washed.

The ultrafilter is a cartridge containing a plurality of tubular/cylindrical ultrafilter membranes. The inner side of an individual tubular/cylindrical ultrafilter membrane is referred to as the core or retentate side of the membrane. The outside of the tubular/cylindrical ultrafilter membrane is referred to as the permeate side of the membrane. The plurality of tubular/cylindrical ultrafilter membranes are contained within a cylindrical cartridge which has a top and bottom cover. The space within the cartridge which surrounding the plurality of tubular/cylindrical ultrafilter membranes is referred to as the permeate space.

The wash water enters the ultrafilter through the core. Fluid entering the cores of the tubular/cylindrical ultrafilter membranes can only enter the permeate space by passing through pores of the ultrafilter membrane. The fluid which passes through the ultrafilter membrane is referred to as filtrate or permeate. Material from the fluid which cannot pass through the membrane, such as particulates which are too large to pass through the pores of the ultrafilter are referred to as retentate. In systems for concentrating or screening and detecting analytes, the analyte is a particulate too large to pass through the ultrafilter membranes such that it becomes part of the retentate. In the produce screening application, for example, particles larger than 25 nm, including the target analyte, such as pathogens, are collected in the retentate using ultrafilter membranes with pores smaller than 25 nm.

In the produce screening system described herein, the pre-filtered raw sample is pumped into the cartridge through one or more sample inlet ports in which the fluid entering such ports enters the ultrafilter membrane cores. The fluid from pre-filtered raw sample passes through the filter to produce a first stage filtrate or first stage permeate and forming a first stage retentate comprising the material unable to pass through the ultrafilter membrane cores of the first stage ultrafilter. The first stage filtrate exits the filter cartridge through one or more permeate exit ports through tubing to either disposal drain, if the filtrate is to be discarded, or to a return line if the filtrate is to be recycled back into the wash water source. Alternatively, the water may be routed to for further processing before recycling, disposing for another use or discarding.

Once the designated sample collection time has elapsed, the collected particles which are in the retentate are removed from the ultrafilter core. The first stage retentate is collected as follows. The water is first removed from the permeate space of the filter. Since no pathogens are retained on the permeate side of the filter, removing this liquid serves to reduce the sample volume by preventing any liquid from reentering the core from the permeate space yielding a more concentrated product. Liquid in the permeate space of the ultrafilter cartridge is removed by allowing it to drain out and be replaced by air which enters the permeate space either through a purge valve which may be opened to allow air to enter the space and displace the liquid which drains out of a filtrate exit port or a drain port by gravity or through the introduction of air into another filtrate exit port opened to allow air to enter the space and displace the liquid which drains out of a filtrate exit port or a drain port by gravity. Alternatively or additionally, a gas such as compressed air may be introduced into the permeate space either through a purge valve to force air to enter the space and displace the liquid which is forced to exit the permeate space through a filtrate exit port or a drain port, or a gas such as compressed air may be introduced into the permeate space though one filtrate exit port to force air to enter the space and dispel the liquid which is forced to exit the permeate space through another filtrate exit port or a drain port. Using a gas such as processed air and a liquid such as filtered tap water, the sample is flushed from the filter core and collected as a retentate solution into a sample holding tank. The cores are flushed using a combination of gas and liquid to remove the retentate from the cores. A gas such as compressed air is introduced into the cores through a sample inlet port or a valve-controlled, core rinsing port. If the gas is introduced into the cores through a sample inlet port, a valve is employed to close the line to the wash tank and restrict gas flow to ensure that sufficient pressure is in the cores to flush the contents from them. If the gas is introduced into the cores through a valve-controlled, core rinsing port, a valve is employed to close the line from the inlet ports to the wash tank and a valve is opened to provide gas flow into the cores to flush the contents from them. Rinse liquid is also introduced into the core though either the same entry points as the gas or separate inlets.

A first retentate solution forms from the liquid retained in the core and the rinse liquid. This first retentate solution is collected from either another sample inlet port which serves as a drain port in the retentate solution collection step, or a valved drain port. If the first retentate solution is collected from another sample inlet port, a valve is employed to close off the line to the wash tank and redirect the drained first retentate solution to a collection line. If the first retentate solution is collected from valved drain port, a valve is employed to close off the line from the any sample inlet ports to the wash tank and open a line to allow the drained first retentate solution to exit the valved drain port and enter a collection line.

Once the first retentate solution is collected, a portion of it, approximately 30%, is pumped through a second stage ultrafilter, which is a 1' ultrafilter, X-Flow model type RX-300 PSU. The membrane diameter is 0.8 mm, the membrane area is 0.07 $m^2$, the length is 300 mm, and the pore is 25-35 nm. After the designated amount of sample first retentate solution has been processed through the second stage ultrafilter, the sample is collected as a second retentate solution in the same manner as described for the first stage 4' ultrafilter. That is, after the first retentate solution has passed though the second stage ultrafilter, a second retentate solution is collected by displacing liquid from the permeate space of the second stage ultrafilter with gas, and rinsing the cores of the second stage ultrafilter with a combination of gas and liquid to produce a second retentate solution that is collected and analyzed for the presence of an analyte.

Just as in the case of the first stage ultrafilter, liquid is first removed from the permeate space of the second stage ultrafilter by allowing it to drain out and be replaced by air which enters the permeate space either through a purge valve which may be opened to allow air to enter the space and displace the liquid which drains out of a filtrate exit port or a drain port by gravity or through the introduction of air into another filtrate exit port opened to allow air to enter the space and displace the liquid which drains out of a filtrate exit port or a drain port by gravity. Alternatively or additionally, a gas such as compressed air may be introduced into the permeate space either through a purge valve to force air to enter the space and displace the liquid which is forced to exit the permeate space through a filtrate exit port or a drain port, or a gas such as compressed air may be introduced into the permeate space though one filtrate exit port to force air to enter the space and dispel the liquid which is forced to exit the permeate space through another filtrate exit port or a drain port. Using a gas such as processed air and a liquid such as filtered tap water, the liquid is flushed from the second stage ultrafilter cores and collected as a second retentate solution and routed to a detection stage for analysis. The cores are flushed using a combination or gas and liquid to remove the retentate from the cores. A gas such as compressed air is introduced into the cores through a sample inlet port or a valve-controlled, core rinsing port. If the gas is introduced into the cores through a sample inlet port, a valve is employed to close the line to the wash tank and restrict gas flow to ensure that sufficient pressure is in the cores to flush the contents from them. If the gas is introduced into the cores through a valve-controlled, core rinsing port, a valve is employed to close the line from the inlet ports to the wash tank and a valve is opened to provide gas flow into the cores to flush the contents from them. Rinse liquid is also introduced into the core though either the same entry points as the gas or separate inlets.

The second stage retentate may represent the final sample which is then processed through an array biosensor, the UltraRapid 6000 (Hanson Technologies, Carlisle, Pa.). The biosensor automatically draws the concentrated sample from the holding tank after receiving a signal that the sample is ready for assay and analysis. During the assay, the sample is screened for the presence of the target pathogens, such as *E. coli* O157:H7. The data is automatically analyzed, and a positive/negative result is reported.

The first stage ultrafilter and the second stage ultrafilter are cleaned in a cleaning cycle following collection of the retentate solution from the respective filter. Cleaning cycles for each stage can commence independently or as part of a coordinated cleaning cycle initiation. Cleaning cycles may be simultaneous or sequential. In this example, immediately after the first ultrafilter completes its portion of the sample processing, the cleaning cycle is initiated. The cleaning cycle uses two chemicals, 3% sodium hydroxide (NaOH) and 3% hydrochloric acid (HCl), and each chemical is contained in a separate tank that connects into the fluidic line leading to the filter. To begin the cleaning protocol, the filter is first completely emptied. The outside of the filter, i.e. the permeate space, is then filled with NaOH and the chemical is pushed through the fibers to fill the core of the filter as well. Once both the outside and core are filled, the filter soaks in the NaOH for 10-15 minutes. After this time, fresh NaOH solution is introduced from the outside of the filter to the core, forcing the used chemical from the core. The filter then enters another soak period of 10-15 minutes. This process continues for several cycles. Upon completion of the NaOH portion of the cleaning, the filter is flushed with filtered tap water from the outside through the filter membrane to the inside core to remove any remaining NaOH solution. The filter is emptied of all liquid, and the cleaning process is repeated using the HCl cleaning solution. The cleaning process is complete once the initial flow rate of the filter is restored. A second protocol is used to flush the tubing, piping, valves, and pumps outside of the filter-to-filter connections, as well as all sample holding tanks and pre-filter housings, with 3% NaOH to ensure any remaining pathogens in the system are removed. In addition to being cleaning with NaOH, the UltraRapid sample holding tank is also filled with a 0.6% sodium hypochlorite solution. This cleaning solution is pumped from the sample tank through the UltraRapid 6000 for sanitization. Following each of the cleaning and sanitization protocols, filtered tap water is used to neutralize any chemicals remaining in the system. The same process is followed to clean the second stage ultrafilter.

Example 2

To allow for continuously sampling of produce, a system parallel to the one previously described in Example 1 is provided as a shown in Figure @@@. Included are one additional first stage 4' ultrafilter for a total of two first stage 4' ultrafilters which each run in parallel with each other, and two additional second stage 1' ultrafilters for a total of three second stage 1' ultrafilters which each run in parallel with each other. In addition, all the necessary pumps, valves, tubing, and connections necessary to move the liquid sample through the system are provided as are the components needed for cleaning cycles. The controls are designed to allow for multiple processes to occur simultaneously. For example, after the wash water from a lot of produce was been sampled through one of 4' ultrafilters, sampling immediately begins on the next lot of produce using the second available 4' ultrafilter. This allows time for the first ultrafilter to be cleaned and regenerated without interrupting the typical operation of produce plant. In addition, the 1' ultrafilters and the UltraRapid 6000 can each process the wash water sample and enter appropriate cleaning cycles independently of the other processes occurring in the system.

Example 3

The components used in Examples 1 and 2 are provided and function as follows:

1. Valves—The one-way directional valves are controlled by the computer program. The valves are used throughout the system.

2. Tubing/piping—The tubing/piping connects the valves, pumps, tanks, and filters, allowing the wash water to flow through the system.

3. Pumps—The diaphragm pumps move liquid by filling a chamber then expelling its contents. The fluid never comes into contact with the mechanical parts of the pump, only the fill chambers. The pumps are turned on and off by the program, and their operation may be controlled by the valves in the same line. The valves maintain pressure in the system when they are closed, and the pump does not force liquid through the valves. When the valves are open, liquid is free to move through the tubing/piping and the pump runs to move as much liquid as possible through the system.

4. Connection to access wash tank—This is a simple threaded connector on the end of a piece of tubing coming from the OmniFresh 1000™ system that screws onto a matched connector on the vegetable washer.

5. Pre-filters—This is a 50 and 10 micron filter set up in series. The filters prevent debris of larger than the rated size of the filter. For example, a 50 micron filter would stop material that is nominally 50 microns or larger from passing through it and allow particles smaller than 50 microns to pass through.

6. 4' ultrafilters—The hollow-fiber ultrafilter stops particles 25 nanometers or larger from passing through it and allows particles smaller than 25 nanometers to pass through. The hollow-fiber filter works by pushing incoming sample into the hollow fibers. The only way for fluid to exit the fibers is to pass through the fiber wall, trapping particles of 25 nanometers or larger inside the fibers. The liquid that passes through the fiber wall then exits the fiber through an exit port and is discarded from the system as excess liquid volume. The hollow-fiber ultrafilter selected for this embodiment is approximately 4 feet tall with a 4 inch diameter and has fibers with a 0.8 millimeter diameter due to its ability to handle more complex, heavily loaded samples. There are two 4' ultrafilters in the system to allow for continuously screening of the produce wash water for pathogens.

7. 1' ultrafilter—The hollow-fiber ultrafilter stops particles 25 nanometers or larger from passing through it and allows particles smaller than 25 nanometers to pass through. The hollow-fiber filter works by pushing incoming sample into the hollow fibers. The only way for fluid to exit the fibers is to pass through the fiber wall trapping particles of 25 nanometers or larger inside the fibers. The liquid that passes through the fiber wall then exits the fiber through an exit port and is discarded from the system as excess liquid volume. The hollow-fiber ultrafilter selected for this embodiment is approximately 1 foot tall with a 1 inch diameter and has fibers with a 0.8 millimeter diameter due to its ability to handle more complex, heavily loaded samples. There are three 1' ultrafilters in the system to allow for continuously screening of the produce wash water for pathogens.

8. UltraRapid 6000—This is the detection unit that automatically draws in sample, screens the sample for specified targets, and analyzes the data.

9. Programmable logic controller—Handles all input/output relays between the computer and the individual valves, pumps and other controlled components. As variation is removed from procedures, the programs to execute the procedures will reside on and be performed from the PLC. The PLC will take direction from the computer to perform the procedures not controlled by the PLC. The actual amount of programming residing on the PLC will be optimized with that on the computer for best performance, reliability, and repeatability. It is possible that all programming will reside on the PLC and the interface would be an integrated touch screen.

10. Computer—The computer is the main interface for the screening system. The integrated program that runs all functions of the vegetable screener is housed here. As variation is removed from procedures, the programs to execute the procedures will be moved from computer control to PLC control. The actual amount of programming residing on the computer will be optimized with that on the PLC for best performance, reliability, and repeatability. It is possible that the computer may be removed from the design if it fits the optimum conditions.

11. Air inlet—Using non-lubricated air and on-board air filtration, the air inlet allows air to be used when flushing out the ultrafilters. The air is also used for pump and valve operation.

12. Water (tap) inlet—The tap water is filtered to 0.2 microns. The inlet allows for tap water to be delivered to the system for flushing and clearing of the system. It is used after sodium hydroxide, hydrochloric acid, and sodium hypochlorite cleaning to remove excess reagent.

13. Cleaning solution tank—Sodium hydroxide (NaOH)—This tank houses the sodium hydroxide solution used to clean the ultrafilters. This solution is necessary to restore filter function back to its original capability before running any sample through it.

14. Cleaning solution tank—Hydrochloric acid—This tank houses the hydrochloric acid solution used to clean the ultrafilters. This solution is necessary to restore filter function back to its original capability before running any sample through it.

15. Cleaning solution tank—Sodium hypochlorite solution—This tank holds the sodium hypochlorite solution that is used to clean and sanitize the UltraRapid sample holding tank and the UltraRapid 6000.

16. Stage 2 sample holding tank—This tank stores the sample water after it has been processed through first 4' ultrafilter. There is one tank for each of the 4' ultrafilters, and any of the three 1' ultrafilters can draw its sample from either tank.

17. UR sample holding tank—This tank holds the concentrated sample processed by the 1' ultrafilter before it is analyzed by the UltraRapid 6000. There is one sample tank shared between the three 1' ultrafilters, and the tank holds only one sample at a time.

18. Chemical waste storage tank—This tank collects and stores all of the cleaning chemicals used throughout the system until proper waste disposal occurs.

Example 4

A system for screening green leafy vegetables, such as spinach, is designed to be employed for testing samples for commercial scale washing equipment. Lots of 2000-3000 pounds are washed with water which is recycled for further wash cycles. The water that is lost due to evaporation, spillage or adherence to washed produce is replaced with new wash water. The pathogen of interest is *E. coli* 0157.H7. In tests, a non-pathogenic form of *E. coli* 0157.H7 is used (e.g. ATCC 43888).

A two stage concentration system may be employed. In the first stage, about 100-150 gallons, preferably 120 gallon sample of used wash water is drawn off continuously during the wash process from the wash tank. The sample of used wash water is processed by the stage 1 ultrafilter to yield. The first stage yields approximately 3 to 30 liters of retentate solution which is further concentrated by a second stage. Generally, a fraction of about 25-50% of the retentate solution is further concentrated. Typically, the second stage concentration step is a smaller version of the first stage. The second stage yields approximately 25-100 mls of concentrated retentate solution which is analyzed for the presence of the analyte. Analysis may be performed by an array biosensor which employs a biochip containing analyte specific ligands, such as antibodies, on its surface. After the concentrated retentate solution is contacted with the biochip surface, the biochip is washed and a second solution comprising an analyte specific ligand is contacted with the biochip. The second analyte specific ligand comprises a detectable label such as a label that emits fluorescent light when activated by evanescent or scatter light which is passed though the biochip. A sensor on the biosensor can detect light. The programmed computer linked to the Example 5

A two stage ultrafiltration system as depicted in FIGS. 3-13 is provided which delivers concentrate to an array biosensor for detection of analytes in a sample liquid. The sample liquid may be wash water from a vegetable washing system. The used wash water in such a system is collected in a wash tank 50. Most of the water in the wash tank 50 is reused in the next vegetable wash cycle. A supply line 51 from wash tank 50 to valve manifold 52 provides for continuous sampling of the used wash water. Water is drawn from wash tank 50 through supply line 51 to valve manifold 52. Prior to concentration, water is passed through a pre-filter station which is preferably a series of two mesh, bag-type filters, one 53 having a cut off size of 50 microns, and the other 54 having a cut off size of 10 microns.

During the stage 1 filtration step, programmed computer 55 signals for valve 74 of valve manifold 64 to be opened, allowing the used wash water to flow into 4' filter 58 through a retentate access port 60 on the filter 58. The programmed computer 55 signals for valve 81 and 82 of valve manifold 65 and valve 89 of valve manifold 66 to be opened. Filtrate flows from the filter 58 through permeate access ports 61 through valves 81 and 82 to a drain line 92 which delivers it to a disposal drain, or, if a customer requires it, a collection tank for another use or for reuse. Filtrate flows from the filter 58 through permeate access ports 62 through valve 89 to a drain line 93 which delivers it to a disposal drain, or, if a customer requires it, a collection tank for another use or for reuse.

The programmed computer 55 initiates a transition from first stage filtration step to the first stage collection step. The transition may be initiated following elapse of a programmed amount of time, or following the flow of a programmed quantity of water which may be determined by an optional flow meter 65 provided on supply line 51, or detection of a programmed pressure in supply line 51 by an optionally provided pressure meter 66 on supply line 51, or following a reduction in flow to a programmed flow level which may be determined by an optional flow meter 67 provided on supply line from permeate access port 61, or detection of a programmed pressure in supply line from permeate access port 61 by an optionally provided pressure meter 68, or following a reduction in flow to a programmed flow level which may be determined by an optional flow meter 67 provided on supply line from permeate access port 61. Typically, 100-400 gallons of wash water flow through the ultrafilter during a stage 1 filtration step.

Upon initiating the stage 1 collection step, flow to the filter 58 is discontinued by the programmed computer 55 signaling valve 74 of valve manifold 64 to be closed. Filtrate in the permeate space of filter 58 is displaced with air as follows. The programmed computer 55 signals valve 88 of valve manifold 66 and valves 81 and 82 of valve manifold 65 to each be open. Valve 82 is connected to drain line 92. Valve 88 is connected to compressed air supply line 95. The programmed computer 55 signals to provide sufficient air flow into the permeate space to clear liquid from the permeate space.

The core flush is initiated by the programmed computer 55 which signals valves 88, 81 and 82 to be closed, and valve 77 of valve manifold 63 and valve 70 of valve manifold 64 to be open. Valve 77 connects the retentate access port 59 to compressed air supply line 96. Valve 70 connects the retentate access port 60 to collection line 101 which connects to stage 2 sample collection tank 102. Upon opening valve 77, air pressure forces contents of the core of filter 55 to the collection line 101 which connects to stage 2 sample collection tank 102. The programmed computer 55 signals valve 78 of valve manifold 63 to open while valve 77 of valve manifold 63 remains open. Valve 78 is connected to tap water supply line 98. Upon opening valve 78, water from tap water supply line 98 enters the core or filter 58 and the air pressure forces the tap water and contents of the core of filter 55 to the collection line 101 which connects to stage 2 sample collection tank 102. The amount of air and water delivered may be controlled by programmed computer 55 based upon time, quantity of water, amount collected or combinations thereof. Typically, between 3 and 10 liters of retentate solution are collected from the core flush of the stage 1 collection step.

Following completion of the stage 1 collection step, the stage 1 cleaning step is initiated. The stage 1 cleaning step includes separate sub-steps which alternately are initiated.

Cleaning sub-steps include a stage 1 water cleaning sub-step, a stage 1 basic solution cleaning sub-step, a first stage 1 water flush and fill sub-step, a stage 1 acid solution cleaning sub-step, and a second stage 1 water flush and fill sub-step.

The first stage water cleaning sub-step is initiated by the programmed computer 55 in which all valves closed except valves 81 and 83 of valve manifold 65, and valve 90 of valve manifold 66. Valves 81 and 83 connect to permeate access port 61 to water supply line 99. Valve 90 is connected to permeate access port 62 and drain line 112 which is connected to waste storage tank 115. Water flows into permeate access port 61 and out of the permeate space though permeate access port 62. The programmed computer 55 signals to close valve 90 and open valve 76 of valve manifold 63. Valve 76 is connected to retentate access port 59 and drain line 113 which is connected to waste storage tank 115. Water flows into permeate access port 61 and back-flushes the filter membranes into retentate space. The water flows out of the retentate space through retentate access port 59 and into waste storage tank 115. Valve 76 is closed and valve 83 of valve manifold 65 and valve 73 of valve manifold 64 are opened. Valve 83 is connected to permeate access port 61 and tap water supply line 99. Valve 73 is connected to permeate access port 60 and drain line 114 which is connected to waste storage tank 115. Typically, the water flows for 10 minutes of 1 minute intervals between the core top and core bottom valves. The filter is preferably then checked to confirm it is not broken. The programmed computer 55 signals to close all valve except valve 88 of valve manifold 66 and valve 73 of valve manifold 64 which are open. Valve 88 is connected to permeate access port 62 and air supply line 95. Valve 73 connects retentate access port 60 to chemical waste line 114 which is connected to waste storage tank 115. Valve 88 is closed and valve 77 of valve manifold 63 which are open. Valve 77 is connected to retentate access port 59 and air supply line 96. Valve 77 is closed and valve 87 of valve manifold 66 which are open. Valve 87 is connected to broke filter out line.

The stage 1 basic solution cleaning sub-steps are initiated by closing valves 87 and 73 and opening valves 81 and 85 of valve manifold 65 and valve 90 of valve manifold 66. Valves 81 and 85 connect permeate access port 61 and chemical clean supply line 108, which contains basic solution such as 3% NaOH. Chemical clean supply line 108 is connected to basic solution reservoir 103 through valve 106 which is connected to supply line 108 by valve 116. Valve 90 is connected to permeate access port 62 and drain line 112 which is connected to waste storage tank 115. The programmed computer 55 opens valves 106 and 116 during the stage 1 basic solution cleaning sub-step. During this substep the permeate space is cleaned. Valve 90 is closed and valve 76 is opened. Valve 76 is connected to retentate access port 59 and drain line 113 which flows into a chemical waste storage tank 115. During this substep, the basic solution back-flushes from the permeate space to the retentate space. Valves 76 and 81 are closed while valve 85 remains opened. During this sub-step of the basic solution cleaning, the ultrafilter soaks in the basic cleaning solution. Typically, the basic solution flows for 30-60 seconds and then the valves are closed and the membranes soak, typically for 10 to 15 minutes. Upon completion of the soak, the filter is flushed with basic solution by opening valves 81 and 73. Valve 73 connects retentate access port 60 to chemical waste line 114 which is connected to waste storage tank 115. Valve 73 is closed and valve 76 is opened. Valve 76 connects retentate access port 59 to chemical waste line 113 which is connected to waste storage tank 115. The basic cleaning solution is then flushed from the retentate space by closing valves 76, 81 and 85 and opening valves 77 and 73. Valve 77 is connected to retentate access port 59 and air supply line 96. Valve 73 connects retentate access port 60 to chemical waste line 114 which is connected to waste storage tank 115. The basic solution is typically 3% NaOH solution pH≥14. Typically 4 to 6 liters of solution are used in a single first stage basic solution cleaning sub-step.

After the completion of the stage 1 basic solution cleaning sub-steps, the stage 1 filter is water flushed and filled. Water enters through the permeate access port and back-flushes through the filter into the retentate space for 30-60 seconds. Air is introduced on the permeate side, back-flushing the permeate contents through the filter to the retentate space. Air is used to remove the liquid in the retentate space. This procedure is repeated five times and results in neutral pH (6.5-8.5). The programmed computer 55 signals all valves closed except valves 81 and 83 of valve manifold 65, and valve 90 of valve manifold 66. Valves 81 and 83 connect to permeate access port 61 to water supply line 99. Valve 90 is connected to permeate access port 62 and drain line 112 which is connected to waste storage tank 115. Water flows into permeate access port 61 and out of the permeate space though permeate access port 62. The programmed computer 55 signals to close valve 90 and open valve 76 of valve manifold 63. Valve 76 is connected to retentate access port 59 and drain line 113 which is connected to waste storage tank 115. Water flows into permeate access port 61 and back-flushes the filter membranes into retentate space. The water flows out of the retentate space through retentate access port 59 and into waste storage tank 115. Valve 76 is closed and valve 83 of valve manifold 65 and valve 73 of valve manifold 64 are opened. Valve 83 is connected to permeate access port 61 and tap water supply line 99. Valve 73 is connected to permeate access port 60 and drain line 114 which is connected to waste storage tank 115. Typically, the water flows for 10 minutes of 1 minute intervals between the core top and core bottom valves. The filter is preferably then checked to confirm it is not broken. The programmed computer 55 signals to close all valve except valve 88 of valve manifold 66 and valve 73 of valve manifold 64 which are open. Valve 88 is connected to permeate access port 62 and air supply line 95. Valve 73 connects retentate access port 60 to chemical waste line 114 which is connected to waste storage tank 115. Valve 88 is closed and valve 77 of valve manifold 63 which are open. Valve 77 is connected to retentate access port 59 and air supply line 96. Valve 77 is closed and valve 87 of valve manifold 66 which are open. Valve 87 is connected to broke filter out line 120.

The stage 1 acid solution cleaning sub-steps are initiated by closing valves 87 and 73 and opening valves 81 and 85 of valve manifold 65 and valve 90 of valve manifold 66. Valves 81 and 85 connect permeate access port 61 and chemical clean supply line 108, which contains acid solution such as 3% HCl. Chemical clean supply line 109 is connected to acid solution reservoir 104 through valve 107 which is connected to supply line 109 by valve 117. Valve 90 is connected to permeate access port 62 and drain line 112 which is connected to waste storage tank 115. The programmed computer 55 opens valves 106 and 116 during the stage 1 acid solution cleaning sub-step. During this sub-step the permeate space is cleaned. Valve 90 is closed and valve 76 is opened. Valve 76 is connected to retentate access port 59 and drain line 113 which flows into a chemical waste storage tank 115. During this sub-step, the acid solution back-flushes from the permeate space to the retentate space. Valves 76 and 81 are closed while valve 85 remains opened. During this sub-step of the acid solution cleaning, the ultrafilter soaks in the acid cleaning solution. Typically, the acid solution flows for 30-60 seconds and then the valves are closed and the membranes soak, typically for 10 to 15 minutes. Upon completion of the soak, the filter is flushed with basic solution by opening valves 81 and 73. Valve 73 connects retentate access port 60 to chemical waste line 114 which is connected to waste storage tank 115. Valve 73 is closed and valve 76 is opened. Valve 76 connects retentate access port 59 to chemical waste line 113 which is connected to waste storage tank 115. The acid cleaning solution is then flushed from the retentate space by closing valves 76, 81 and 85 and opening valves 77 and 73. Valve 77 is connected to retentate access port 59 and air supply line 96. Valve 73 connects retentate access port 60 to chemical waste line 114 which is connected to waste storage tank 115. The acidic solution is typically 3% HCl solution pH≤1. Typically 4 to 6 liters of solution are used in a single first stage acidic solution cleaning sub-step.

Following the cleaning step, the system is ready for resuming filtration.

The stage 2 concentration is initiated either upon completion of the stage 1 filtration, a period of time has elapsed following the completion of the stage 1 filtration, or when sufficient amount of retentate solution is collected from the stage 1. Typically about 30% of the collected retentate solution is used in the stage 2 filtration step.

Typically, one to two liters of retentate solution from the first stage concentration flow through the ultrafilter during a second stage filtration step.

Prior to the stage 2 filtration step, programmed computer 55 purges the pump line by signaling s for valves 142 of valve manifold 128 and valve 143 and valve 147 of valve manifold 129 to be opened. Valve 147 is connected to the stage 2 sample collection tank 102 by supply line 149 which passes through valve 150. Valve 142 is connected to the stage 2 sample collection tank 102 by drain line 151.

During the stage 2 filtration step, programmed computer 55 signals for valve 142 to be closed and valve 134 and valve 135 of valve manifold 127 to be opened. Valves 134 and 135 connect to filter 121 through permeate access port 123. Sample from stage 2 sample collection tank 102 passes through valves 147 and 143, enters the filter through retentate access port 125 and filtrate exits permeate access port 123, passes though valve 134 and exits valve 135 to drain line 152 which delivers it to a disposal drain, or, if the customer requires, a collection tank for another use or for reuse.

The programmed computer 55 initiates a transition from stage 2 filtration step to the stage 2 collection step. The transition may be initiated following elapse of a programmed amount of time, or following the flow of a programmed quantity of water which may be determined by an optional flow meter 153 provided on supply line 149, or detection of a programmed pressure in supply line 149 by an optionally provided pressure meter 154 on supply line 149, or following a reduction in flow to a programmed flow level which may be determined by an optional flow meter 153 provided on supply line 149, or detection of a programmed pressure in drain line 152 by an optionally provided pressure meter 155 on drain line 152, or following a reduction in flow to a programmed flow level which may be determined by an optional flow meter 156 provided on drain line 152. Typically, 1-2 liters of retentate solution from the first stage concentration flow through the ultrafilter during a second stage filtration step.

Upon initiating the stage 2 collection step, flow to the filter 121 is discontinued by the programmed computer 55 signaling valve 143 and valve 144 of valve manifold 129 to be closed. Filtrate in the permeate space of filter 121 is displaced with air as follows. The programmed computer 55 signals valve 131 of valve manifold 126 to be open. Valve 134 and valve 135 of valve manifold 127 remain open. Valve 135 is connected to drain line 152. Valve 131 is connected to compressed air supply line 157. The programmed computer 55 signals to provide sufficient air flow into the permeate space to clear liquid from the permeate space.

The core flush is initiated by the programmed computer 55 which signals valves 131, 134 and 135 to be closed. The programmed computer 55 signals valve 139 of valve manifold 128, valve 143 and valve 148 of valve manifold 129 to each open. Valve 139 connects the retentate access port 124 to compressed air supply line 158. Valve 148 connects the retentate access port 125 to sample collection vessel 159. Upon opening of valves 139, 143 and 148, the air flushes the contents of the retentate space out of the filter and into the collection vessel. Valve 138 is opened. Valve 138 connects retentate access port 124 to tap water supply line 160. Upon opening of valves 138, the tap water and air flushes the contents of the retentate space out of the filter and into the collection vessel. The amount of air and water delivered may be controlled by programmed computer 55 based upon time, quantity of water, amount collected or combinations thereof. Typically, between 50-85 ml of retentate solution are collected from the core flush of the second stage collection step.

Following completion of the stage 2 collection step, the stage 2 cleaning step is initiated. The stage 2 cleaning step includes separate sub-steps which are alternately initiated. Cleaning sub-steps include a stage water 2 cleaning, a stage 2 basic solution cleaning sub-step, a first stage 2 water flush and fill sub-step, a stage 2 acid solution cleaning sub-step, and a second stage 2 water flush and fill sub-step.

The stage 2 water cleaning sub-step is initiated by filling the permeate. Valves 138, 139, 143 and 148 are closed and valves 134, 136 and 133 are opened. Valve 136 connects permeate access port 123 to tap water supply line 161. Valve 133 connects permeate access port 122 to chemical waste line 162. The filter is then back-flushed by closing valve 133 and opening valve 141 which is connected to chemical waste line 163. Valve 141 is then closed and valves 143 and 144 are opened. Valve 144 connects retentate access port 125 to chemical waste line 164. Typically, the water flows for 10 minutes of 1 minute intervals between the core top and core bottom valves and is flushed into a chemical waste storage tank. At this time a broke filter check is done by closed valves 134 and 136 and opening valve 131. Valve 131 connects permeate access port 122 to air supply line 165. Valve 131 is closed and valve 139 is opened. Valve 139 connects retentate access port 124 to air supply line 158. The broke filter check is completed by closing valve 139 and opening valve 132 which is connected to broke filter check 166.

The stage 2 basic solution cleaning sub-steps are initiated by closing valves 132, 143 and 144 and opening valve 133 of valve manifold 126, valve 134 and valve 137 of valve manifold 127. Valve 133 is connected to permeate access port 122 and chemical waste line 167 which is connected to waste storage tank 115. Valve 137 is connected to permeate access port 123 and chemical supply line 110. During this substep the permeate space is cleaned. Valves 134 and 137 connect permeate access port 123 and chemical clean supply line 110, which contains basic solution such as 3% NaOH. Chemical clean supply line 110 is connected to basic solution reservoir 103 through valve 106 which is connected to supply line 110 by valve 118. The programmed computer 55 opens valves 106 and 118 during the stage 2 basic solution cleaning substep. Valve 133 is closed and valve 141 is opened. Valve 141 connect the retentate access port 124 to chemical waste line 163. During this substep the retentate space is cleaned by back-flushing basic cleaning solution through the filter membrane from the permeate space into the retentate space. Valve 134 and 141 are closed and filter soaks. The basic solution is typically 3% NaOH solution pH≥14. Typically 1-2 liters of solution are used in a single stage basic 2 solution cleaning sub-step.

Second stage water flush and fill. Water enters through the permeate access port and back-flushes through the filter into the retentate space for 30-60 seconds. Air is introduced on the permeate side, back-flushing the permeate contents through the filter to the retentate space. Air is used to remove the liquid in the retentate space. This is repeated five times. Results in neutral pH (6.5-8.5). The first stage 2 water cleaning and fill sub-step is initiated by filling the permeate. Valves 138, 139, 143 and 148 are closed and valves 134, 136 and 133 are opened. Valve 136 connects permeate access port 123 to tap water supply line 161. Valve 133 connects permeate access port 122 to chemical waste line 162. The filter is then back-flushed by closing valve 133 and opening valve 141 which is connected to chemical waste line 163. Valve 141 is then closed and valves 143 and 144 are opened. Valve 144 connects retentate access port 125 to chemical waste line 164. Typically, the water flows for 10 minutes of 1 minute intervals between the core top and core bottom valves and is flushed into a chemical waste storage tank. At this time a broke filter check may be done by closed valves 134 and 136 and opening valve 131. Valve 131 connects permeate access port 122 to air supply line 165. Valve 131 is closed and valve 139 is opened. Valve 139 connects retentate access port 124 to air supply line 158. The broke filter check is completed by closing valve 139 and opening valve 132 which is connected to broke filter check 166.

The stage 2 acid solution cleaning sub-steps are initiated by closing valves 132, 143 and 144 and opening valve 133 of valve manifold 126, valve 134 and valve 137 of valve manifold 127. Valve 133 is connected to permeate access port 122 and chemical waste line 167 which is connected to waste storage tank 115. Valve 137 is connected to permeate access port 123 and chemical supply line 111. During this substep the permeate space is cleaned. Valves 134 and 137 connect permeate access port 123 and chemical clean supply line 111, which contains basic solution such as 3% HCl. Chemical clean supply line 111 is connected to acidic solution reservoir 104 through valve 107 which is connected to supply line 111 by valve 119. The programmed computer 55 opens valves 107 and 119 during the stage 2 acidic solution cleaning substep. Valve 133 is closed and valve 141 is opened. Valve 141 connect the retentate access port 124 to chemical waste line 163. During this substep the retentate space is cleaned by back-flushing acidic cleaning solution through the filter membrane from the permeate space into the retentate space. Valve 134 and 141 are closed and filter soaks. Typically, the acidic solution flows for 30-60 seconds and then the valves are closed and the membranes soak, typically for 10-15 minutes. Upon completion of the soak, the acidic solution is flushed though the drain line into a chemical waste storage tank. The acidic solution is typically 3% HCl solution pH≤1. Typically 1-2 liters of solution are used in a single second stage acidic solution cleaning sub-step.

The second stage 2 water cleaning and fill sub-step is initiated by filling the permeate. Valves 138, 139, 143 and 148 are closed and valves 134, 136 and 133 are opened. Valve 136 connects permeate access port 123 to tap water supply line 161. Valve 133 connects permeate access port 122 to chemical waste line 162. The filter is then back-flushed by closing valve 133 and opening valve 141 which is connected to chemical waste line 163. Valve 141 is then closed and valves 143 and 144 are opened. Valve 144 connects retentate access port 125 to chemical waste line 164. Typically, the water flows for 10 minutes of 1 minute intervals between the core top and core bottom valves and is flushed into a chemical waste storage tank. At this time a broke filter check may be done by closed valves 134 and 136 and opening valve 131. Valve 131 connects permeate access port 122 to air supply line 165. Valve 131 is closed and valve 139 is opened. Valve 139 connects retentate access port 124 to air supply line 158. The broke filter check is completed by closing valve 139 and opening valve 132 which is connected to broke filter check 166.

The retentate solution collected from the core flush of the second stage collection step flows directly to array biosensor or to a collection vessel which is connected to array biosensor. Array biosensor has six channels through which sample can flow over waveguides comprising detection ligands. The waveguide comprises on its surface an antibody which specifically binds to the analyte such that when liquid flows in the channel, it is contacted with the wave guide surface and antibodies attached thereto. In this example, the retentate solution flows through a single channel and a second channel is used for a control. The remaining four channels are reserved for use with subsequently produced sample concentrates. Accordingly, the fluidics are designed and programmed computer is programmed to direct flow over channels being used for a specific test sequence. The test sequence sub-steps include a first wash sub-step, a sample exposure sub-step, a second wash sub-step, a tracer exposure sub-step, and a third wash sub-step.

Before the sample has flowed over the biosensor test sample and negative control channels, the channels are washed. The programmed computer signals to open valves to allow flow of wash fluid from a wash fluid supply over the channels. The wash fluid exits the channels through the exit line. Valves are opened by the programmed computer to allow flow of the wash fluid to a chemical waste disposal line.

For the sample exposure sub-step, the concentrated retentate solution is delivered to the biosensor test sample valve manifold. The programmed computer signals one of the three valves to be opened to flow sample in one of three biosensor test sample channels. The test sample is collected after it exits channel for storage by opening a valve from the exit line at the end of the channel to a sample collection line. The control solution is delivered from the control solution storage tank to the biosensor control valve manifold. The programmed computer signals one of the three valves to be opened to flow control sample in one of three biosensor control channels. The control sample is collected after it exits channel for disposal by opening a valve from the exit line at the end of the channel to a chemical waste disposal line.

After the sample has flowed over the biosensor test sample channel, the channel is washed during the second wash sub-step. The programmed computer signals to close the valve that was opened to deliver the test sample to the channel and opens valve to allow flow of wash fluid from a wash fluid supply over the channel. The wash fluid exits the channel through the exit line. Valve is opened by the programmed computer to allow flow of the wash fluid to a chemical waste disposal line. The programmed computer similarly signals to close the valve that was opened to deliver the control sample to the channel and opens valve to allow flow of wash fluid from a wash fluid supply over the channel. The wash fluid exits the channel through the exit line. Valve is opened by the programmed computer to allow flow of the wash fluid to a chemical waste disposal line.

After the channel has been washed, a solution comprising a tracer enters the channel during the tracer exposure sub-step. The tracer is an antibody that binds to the analyte and comprises a functional element which can be detected. In this example, the functional element is a fluorescent label which can be activated by evanescent or scattered light passing through the wave guide. The tracer solution is maintained in a tracer solution tank which is connected to a tracer supply line which is connected to a valve in a biosensor valve manifold. The programmed computer signals to close the valve that was opened to deliver wash fluid to the channel and opens valve to allow flow of tracer solution from the tracer solution tank over the channel. The tracer solution exits the channel through the exit line. Valve is opened by the programmed computer to allow flow of the tracer solution to a chemical waste disposal line. The programmed computer similarly signals to close the valve that was opened to deliver the wash fluid to the channel used for control and opens valve to allow flow of tracer solution from a tracer solution tank over the control channel. The tracer solution exits the channel through the exit line. Valve is opened by the programmed computer to allow flow of the tracer solution to a chemical waste disposal line.

After the tracer has flowed over the biosensor sample and control channels, the channels are washed during the third wash sub-step. The programmed computer signals to close the valves that were opened to deliver the tracer to the channels and opens valves to allow flow of wash fluid from a wash fluid supply over the channels. The wash fluid exits the channels through the exit line. Valves are opened by the programmed computer to allow flow of the wash fluid to a chemical waste disposal line.

After the third wash sub-step, a light is used to produce evanescence and scattered light in the wave guide. The evanescent and scattered light energy in the wave guide is sufficient to cause fluorescence by label on any tracer antibodies bound to analyte that may be bound to the waveguide. Accordingly, detection of fluorescence indicates analyte in the sample. The biosensor includes fluorescence detection components which are linked to the programmed computer. The programmed computer collects the fluorescence data from both the test sample channel and control sample and thus determines the presence of analyte in the sample.

After completion of testing of a sample by the biosensor, the programmed computer initiates a cleaning process of the biosensor fluidics. The cleaning process sub-steps include a sodium hypochlorite sub-step, a water rinse sub-step, and an air sub-step.

Example 6

The system described in Example 5 may be modified to include two 4' ultrafilters in parallel for the first stage concentration and two or more 1' ultrafilters in parallel for the second stage concentration. According to this design, the supply line from the wash tank is connected to a valve manifold in which supply can be directed through valves to either one of the two 4' ultrafilters in parallel for the first stage concentration. The programmed computer maintains one valve open and one valve closed, thus directing flow to one of the two 4' ultrafilters in parallel for the first stage concentration. When the filtration step is completed for the filter into which flow has been directed, the programmed computer activates the valve to close the valve to which flow was directed and opening the previously closed valve, thereby redirecting flow to the second of the two 4' ultrafilters in parallel for the first stage concentration, while the collection step is initiated in the first of the two 4' ultrafilters in parallel for the first stage concentration. This procedure provides for continuous sampling of the wash tank.

Similarly, the supply line from the first stage collection tank is connected to a valve manifold in which supply can be directed through valves to either one of the two or more 1' ultrafilters in parallel for the second stage concentration. The programmed computer maintains one valve open and the other valves closed, thus directing flow to one of the 1' ultrafilters in parallel for the first stage concentration. When the filtration step is completed for the filter into which flow has been directed, the programmed computer activates the valve to close the valve to which flow was directed and opening one of the previously closed valves, thereby redirecting flow to another one of the two or more 1' ultrafilters in parallel for the first stage concentration, while the collection step is initiated in the first of the 1' ultrafilters in parallel for the first stage concentration.

Example 7

Water is passed through a pre-filtering station that comprises two bag style mesh prefilters, one filtering out particulates larger than 50 microns and a second filtering out particulates larger than 10 microns to effectively remove particulates down to 10 microns. The filtered water continues through an air operated double diaphragm pump {ALL-FLO PT05-A42), through a Process Valve then to the pressure regulator (SMC SRH4010-N04). The system processes the water using distribution manifolds (material: Unefone PSU) with high purity Fluoropolymer Hyperflare fittings (SMC), Teflon tubing, air operated chemical valves (SMC LVQ40-Z13N-9) and a High Purity Air Processor System (HPAPS, SMC AF40-N03C-Z). The HPAPS also includes a 5 micron filter (AFD40-NO3C-Z), 1 micron micro mist filter (AMG350-NO3C), ambient dryer and membrane air dryer (IDG30-NO3—P).

Sample water continues its flow to a Process Valve. When activated it will allow flow to enter stage 1 core bottom distribution manifold and stage 1 filter. Sample water enters filter core (using pressure supplied from ALL-FLO pump) and permeates through filter membrane. All particulate in sample water larger than 25 to 35 nanometers will be detained in membrane filter tube. Processed water will exit the filter via permeate exit ports top and bottom stage 1 filter (two PVs). The retained particles will be extracted from the core of stage 1 filter by the following process.

The core of stage 1 filter contains the sample to be extracted. With all process valves closed to the stage 1 filter core, the water is then removed from the filter jacket. To accomplish this, permeate to waste flow is enabled (turn on PV (HPAPS access, set to 30 psi)). Air is allowed to enter the stage 1 permeate distribution manifold top (turn on PV). The air flow enters the filter top permeate side and exits through the permeate to waste valve (PV) removing the water to waste. This water is considered to be non-hazardous waste. The process of using air to remove the water on the permeate side generates a turbulent action around the filter tubes helping dislodge particulate on the inside of filter tube surface for extraction. However, there is no transfer of liquid through the membrane because its valves are closed and allows for no trans-element displacement. Removing the water on the permeate side of filter also eliminates dilution of the sample during the core extraction process.

The process to extract the isolated sample from stage 1 filter requires that the liquid retained in the core is collected.

To accomplish this, the system must allow the sample to move from the stage 1 filter core to the stage 2 holding container (turn on PV, turn on PV (HPAPS access, set to 30 psi)). Facilitating the sample collection is air passing through the core top distribution manifold and entering the stage 1 filter core top. When the air pushes through the filter core, it removes the filter core contents and transfers it to the stage 2 holding container. The sample volume size held in the stage 2 holding container will be ~2.5 liters.

Of the ~2.5 liters of sample held in the stage 2 holding container. Stage 2 will process 33% of the volume. The process for stage 2 will be, turn on pump (ALL-FLO PT05-A42, PV), sample enters pressure regulator (SMC SRH4000-N04), stage 2 core bottom distribution manifold. Sample then enters filter core (using pressure supplied from ALL-FLO pump) and permeates through filter membrane—All particulate in sample larger than 25 to 35 nanometers will be detained in membrane filter tube. Processed water will exit the filter via the permeate exit port on top stage 2 filter (PV). The retained particles will be extracted by the following process.

The sample is then collected beginning with all of the stage 2 filter core process valves being closed. At this point, the stage 2 filter core contains the sample to be extracted. The sequence necessary for this is to allow permeate to waste (turn on PV), air to enter permeate top distribution manifold (turn on PV, PV (HPAPS access, set to 30 psi)). The air enters the filter top permeate side and removes water (through PV) to waste. This water is considered to be non-hazardous waste. The process of using air to remove the water on the permeate side generates a turbulent action around the filter tubes helping dislodge particulate on the inside of filter tube surface for extraction. However, there is no transfer of liquid through the membrane because its valves are closed and allows for no trans-element displacement. Removing the water on the permeate side of filter also eliminates dilution of the sample during core extraction process.

The process to extract the isolated sample from stage 2 filter involves allowing sample to move to the next stage (turn on PV) and having the air entering the core top distribution manifold which has access to stage 2 filter core top (turn on PV (HPAPS access, set to 30 psi)) thereby removing the filter core contents and transferring it to HLAB biosensor holding container. The sample volume size will be ~53 milliliters.

Table I

TABLE I

| Example analytes of interest include the following: |
|---|
| Bacteria |
| *Corynebacteria* |
| *Corynebacterium diptheriae* |
| *Pneumococci* |
| *Diplococcus pneumoniae* |
| *Streptococci* |
| *Streptococcus pyogenes* |
| *Streptococcus salivarus* |
| *Staphylococci* |
| *Staphylococcus aureus* |
| *Staphylococcus albus* |
| *Neisseriae* |
| *Neisseria meningitidis* |
| *Neisseria gonorrheae* |
| *Enterobacteriaciae* |
| The coliform bacteria |
| *Escherichia coli* |
| *Aerobacter aerogenes* |
| *Klebsiella pneumoniae* |

TABLE I-continued

| Example analytes of interest include the following: |
|---|
| The *Salmonellae* |
| *Salmonella typhosa* |
| *Salmonella choleraesuis* |
| *Salmonella typhimurium* |
| The *Shigellae* |
| *Shigella dysenteriae* |
| *Shigella schmitzii* |
| *Shigella arabinotarda* |
| *Shigella flexneri* |
| *Shigella boydii* |
| *Shigella Sonnei* |
| Other enteric *bacilli* |
| *Proteus* species |
| *Proteus vulgaris* |
| *Proteus mirabilis* |
| *Proteus morgani* |
| *Pseudomonas aeruginosa* |
| *Alcaligenes faecalis* |
| *Vibrio cholerae* |
| *Hemophilus-Bordetella* group |
| *Hemophilus influenzae* |
| *H. ducreyi* |
| *H. hemophilus* |
| *H. aegypticus* |
| *H. parainfluenzae* |
| *Bordetella pertussis* |
| *Pasteurellae* |
| *Pasteurella pestis* |
| *Pasteurella tulareusis* |
| *Brucellae* |
| *Brucella melitensis* |
| *Brucella abortus* |
| *Brucella suis* |
| Aerobic Spore-forming *Bacilli* |
| *Bacillus anthracis* |
| *Bacillus subtilis* |
| *Bacillus megaterium* |
| *Bacillus cereus* |
| Anaerobic Spore-forming *Bacilli* |
| *Clostridium tetani* |
| *Clostridium perfringens* |
| *Clostridium novyi* |
| *Clostridium septicum* |
| *Clostridium histolyticum* |
| *Clostridium tertium* |
| *Clostridium bifermentans* |
| *Clostridium sporogenes* |
| *Mycobacteria* |
| *Mycobacterium tuberculosis hominis* |
| *Mycobacterium bovis* |
| *Mycobacterium avium* |
| *Mycobacterium leprae* |
| *Mycobacterium paratuberculosis* |
| *Actinomycetes* (fungus-like bacteria) |
| *Actinomyces israelii* |
| *Actinomyces bovis* |
| *Actinomyces naeslundii* |
| *Nocardia asteroides* |
| *Nocardia brasiliensis* |
| The *Spirochetes* |
| *Treponema pallidum* |
| *Spirillum minus* |
| *Treponema pertenue* |
| *Streptobacillus moniliformis* |
| *Treponema carateum* |
| *Borrelia recurrentis* |
| *Leptospira icterohemorrhagiae* |
| *Leptospira canicola* |
| *Mycoplasmas* |
| *Mycoplasma pneumoniae* |
| Other pathogens |
| *Listeria monocytogenes* |
| *Erysipelothrix rhusiopathiae* |
| *Streptobacillus moniliformis* |
| *Donvania granulomatis* |
| *Bartonella bacilliformis* |

TABLE I-continued

Example analytes of interest include the following:

*Rickettsiae* (bacteria-like parasites)
    *Rickettsia prowazekii*
    *Rickettsia mooseri*
    *Rickettsia rickettsii*
    *Rickettsia conori*
    *Rickettsia australis*
    *Rickettsia sibiricus*
    *Rickettsia akari*
    *Rickettsia tsutsugamushi*
    *Rickettsia burnetii*
    *Rickettsia quintana*
    *Coxiella burneti*
*Cyanobacteria* (Cyanotoxin)

Fungi

*Cryptococcus neoformans*
*Blastomyces dermatidis*
*Histoplasma capsulatum*
*Coccidioides immitis*
*Paracoccidioides brasiliensis*
*Candida albicans*
*Aspergillus fumigatus*
*Mucor corymbifer* (*Absidia corymbifera*)
*Tinea*
*Pneumocystis jirovecii*
*Phycomycetes*
    *Rhizopus oryzae*
    *Rhizopus arrhizus*
    *Rhizopus nigricans*
        *Sporotrichum schenkii*
        *Fonsecaea pedrosoi*
        *Fonsecaea compacta*
        *Fonsecae dermatidis*
        *Cladosporium carrionii*
        *Phialophora verrucosa*
        *Aspergillus nidulans*
        *Madurella mycetomi*
        *Madurella grisea*
        *Allescheria boydii*
        *Phialosphora jeansilmei*
        *Microsporum gypseum*
        *Trichophyton mentagrophytes*
        *Keratinomyces ajelloi*
        *Microsporum canis*
        *Trichophyton rubrum*
        *Microsporum adnouini*

Viruses

Adenoviruses
Herpes Viruses
    Herpes simplex
    Varicella (Chicken pox)
    Herpes Zoster (Shingles)
    Virus B
    Cytomegalovirus
Pox Viruses
    Variola (smallpox)
    Vaccinia
    Poxvirus bovis
    Paravaccinia
    Molluscum contagiosum
Picaornaviruses
    Poliovirus
    Coxsackievirus
    Echoviruses
    Rhinoviruses
Myxoviruses
    Influenza (A, B, and C)
    Parainfluenza (1-4)
    Mumps Virus
    Newcastle Disease Virus
    Measles Virus
    Rinderpest Virus
    Canine Distemper Virus
    Respiratory Syncytial Virus
    Rubella Virus
Arboviruses
    Eastern Equine Eucephalitis Virus
    Western Equine Eucephalitis Virus
    Sindbis Virus
    Chikugunya Virus
    Semliki Forest Virus
    Mayora Virus
    St. Louis Encephalitis Virus
    California Encephalitis Virus
    Colorado Tick Fever Virus
    Yellow Fever Virus
    Dengue Virus
Reoviruses
    Reovirus Types 1-3
Hepatitis
    Hepatitis (A, B, C, D, and E) Virus
Tumor Viruses
    Rauscher Leukemia Virus
    Gross Virus
    Maloney Leukemia Virus
    Epstein Barr Virus
Human Immunodeficiency Virus Protozoa

*Balatidium coli*
*Eimeria* species
*Cryptosporidium* species
*Giardia lamblia*
*Toxoplasma* species
*Plasmodium*
*Trypanosoma cruzi*

Dinoflagellates

*Pfiesteria*
*Karenia brevis* (Brevetoxin)
*Alexandrium* species (*Saxitoxins* and *Gonyautoxins*)
*Gambierdiscus toxicus* (Ciguatoxin)
*Dinophysis* species (Okadaic Acid)
*Prorocentrum lima* (Okadaic Acid)

Diatoms

Pseudo-nitzschia (Domoic Acid)

Other Parasites

Dog Heart Worm (*microfilaria*)
Malaria
*Schistosomiasis*
*Coccidosis*
*Trichinosis*
*Chlamydia*
*Ascariasis lumbricoides*
*Sarcocystiasis* species
Roundworm
Tapeworm

The invention claimed is:

1. A method of concentrating an analyte that is in liquid comprising:

a) forming a retentate that contains an analyte by passing a liquid that contains an analyte through a stage 1 ultrafilter membrane that the analyte cannot pass through, wherein the stage 1 ultrafilter membrane has a retentate side on which the liquid that contains the analyte is contacted and a permeate side from which a filtrate exits upon passing through the stage 1 ultrafilter membrane; and, b) collecting the retentate by i) displacing filtrate from the permeate side of the stage 1 ultrafilter membrane with a gas to remove liquid and introduce gas into the permeate side prior to collecting retentate, and ii) collecting retentate by flushing the retentate side of the stage 1 ultrafilter membrane with gas and with liquid to produce a retentate solution that comprises the retentate, and iii) collecting the retentate solution.

2. The method of claim 1 wherein the stage 1 ultrafilter membrane has a pore size of between 1 nm and 10,000 nm.

3. The method of claim 1 wherein the gas is compressed air.

4. The method of claim 1 wherein a concentrated retentate solution with an increased concentration of analyte is produced from the analyte in the retentate solution.

5. The method of claim 1 wherein a concentrated retentate solution with an increased concentration of analyte is produced from the analyte in the retentate solution by the steps of:

forming a concentrated retentate by passing the retentate solution through a stage 2 ultrafilter membrane that the analyte cannot pass through, wherein the stage 2 ultrafilter membrane has a retentate side on which the liquid that contains the analyte is contacted and a permeate side from which a filtrate exits upon passing through the stage 2 ultrafilter membrane;

collecting the concentrated retentate by displacing filtrate from the permeate side of the stage 2 ultrafilter membrane with a gas to remove liquid and introduce gas into the permeate side prior to collecting concentrated retentate, and flushing the retentate side of the stage 2 ultrafilter membrane with gas and with liquid to produce a concentrated retentate solution that comprises the concentrated retentate, and collecting the concentrated retentate solution.

6. The method of claim 5 wherein the stage 2 ultrafilter membrane has a pore size of between 1 nm and 10,000 nm.

7. The method of claim 5 wherein the gas is compressed air.

8. A method of detecting an analyte comprising concentrating an analyte that is in liquid according to claim 5 and detecting analyte in the concentrating retentate solution.

9. A method of detecting an analyte comprising concentrating an analyte that is in liquid according to claim 1 and detecting analyte in the retentate solution.

10. A method of screening a liquid for the presence of an analyte comprising:

a) forming a retentate that contains an analyte by passing a liquid through a stage 1 ultrafilter membrane that the analyte cannot pass through, wherein the stage 1 ultrafilter membrane has a retentate side on which the liquid is contacted and a permeate side from which a filtrate exits upon passing through the stage 1 ultrafilter membrane;

b) collecting the retentate by i) displacing filtrate from the permeate side of the stage 1 ultrafilter membrane with a gas to remove liquid and introduce gas into the permeate side prior to collecting retentate, and ii) collecting retentate by flushing the retentate side of the stage 1 ultrafilter membrane with gas and with liquid to produce a retentate solution that comprises the retentate, and iii) collecting the retentate solution; and c) screening retentate solution for presence of analyte.

11. A method of screening a liquid for the presence of an analyte comprising:

a) forming a retentate that contains an analyte by passing a liquid through a stage 1 ultrafilter membrane that the analyte cannot pass through, wherein the stage 1 ultrafilter membrane has a retentate side on which the liquid is contacted and a permeate side from which a filtrate exits upon passing through the stage 1 ultrafilter membrane;

b) collecting the retentate by i) displacing filtrate from the permeate side of the stage 1 ultrafilter membrane with a gas to remove liquid and introduce gas into the permeate side prior to collecting retentate, and ii) collecting retentate by flushing the retentate side of the stage 1 ultrafilter membrane with gas and with liquid to produce a retentate solution that comprises the retentate, and iii) collecting the retentate solution;

c) forming a concentrated retentate solution; and d) screening the concentrated retentate solution for presence of analyte.

12. The method of claim 11 wherein the concentrated retentate solution is screened for presence of analyte using a biosensor.

13. The method of claim 11 wherein concentrated retentate solution is formed by i) passing the retentate solution through a stage 2 ultrafilter membrane that the analyte cannot pass through, wherein the stage 2 ultrafilter membrane has a retentate side on which the retentate solution is contacted and a permeate side from which a filtrate exits upon passing through the stage 2 ultrafilter membrane;

ii) displacing filtrate from the permeate side of the stage 2 ultrafilter membrane with a gas to remove liquid and introduce gas into the permeate side prior to collecting concentrated retentate, and iii) collecting concentrated retentate by flushing the retentate side of the stage 2 ultrafilter membrane with gas and with liquid to produce a concentrated retentate solution, and iv) collecting the concentrated retentate solution.

14. A process comprising the steps of:

a) performing one or more process cycles wherein each process cycle uses a quantity of fluid, wherein a fraction of the quantity of fluid is lost during the process cycle and a fraction of the quantity of fluid is recovered for reuse with new fluid in a subsequent process cycle;

b) continuously collecting a sample of fluid throughout the process; wherein the sample is collected from the fraction of the quantity of fluid that is recovered for reuse; and c) analyzing the sample to determine whether an analyte is present in the sample;

wherein each process cycle comprises the steps of i) forming a retentate that contains an analyte by passing a liquid that contains an analyte through a stage 1 ultrafilter membrane that the analyte cannot pass through, wherein the stage 1 ultrafilter membrane has a retentate side on which the liquid that contains the analyte is contacted and a permeate side from which a filtrate exits upon passing through the stage 1 ultrafilter membrane; and, ii) collecting the retentate by displacing filtrate from the permeate side of the stage 1 ultrafilter membrane with a gas to remove liquid and introduce gas into the permeate side prior to collecting retentate, and collecting retentate by flushing the retentate side of the stage 1 ultrafilter membrane with gas and with liquid to produce a retentate solution that comprises the retentate, and collecting the retentate solution, and wherein said fluid is said liquid used to flush retentate side of the stage 1 ultrafilter membrane.

15. The process of claim 14 the fluid is a liquid.

16. The process of claim 15 wherein a process cycle comprises contacting one or more solid objects with said quantity of liquid.

17. The process of claim 15 wherein a process cycle comprises combining in a container said quantity of liquid and a quantity of additional liquid to produce a quantity of combined liquid, and removing a fraction of the quantity of combined liquid from said container.

18. The process of claim 14 wherein a process cycle comprises contacting one or more solid objects with said quantity of fluid.

19. The process of claim 14 wherein a process cycle comprises combining in a container said quantity of fluid and a quantity of additional fluid to produce a quantity of combined fluid, and removing a fraction of the quantity of combined fluid from said container.

20. The process of claim 14 wherein at least three process cycles are performed.

21. A process comprising
  a) passing a first sample of liquid through a stage 1 ultrafilter membrane;
  b) collecting retentate from the stage 1 ultrafilter membrane by
    i) displacing filtrate from the permeate side of the stage 1 ultrafilter membrane with a gas to remove liquid and introduce gas into the permeate side prior to collecting retentate, and
    ii) collecting retentate by flushing the retentate side of the stage 1 ultrafilter membrane with gas and with liquid to produce a retentate solution that comprises the retentate, and
    iii) collecting the retentate solution;
  c) washing the stage 1 ultrafilter membrane with an acidic solution;
  d) passing a second sample of liquid through the stage 1 ultrafilter membrane; and
  e) collecting retentate from the stage 1 ultrafilter membrane by
    i) displacing filtrate from the permeate side of the stage 1 ultrafilter membrane with a gas to remove liquid and introduce gas into the permeate side prior to collecting retentate, and
    ii) collecting retentate by flushing the retentate side of the stage 1 ultrafilter membrane with gas and with liquid to produce a retentate solution that comprises the retentate, and
    iii) collecting the retentate solution.

22. The process of claim 21 wherein the acidic solution is hydrochloric acid solution.

23. The method of claim 1 wherein the retentate solution is collected from a retentate access port.

24. The method of claim 23 wherein the filtrate from the permeate side of the stage 1 ultrafilter membrane is flushed with gas using one or more permeate access ports to drain filtrate and supply gas to the permeate side of the stage 1 ultrafilter membrane.

25. The method of claim 23 wherein the retentate side of the stage 1 ultrafilter membrane is flushed with gas and with liquid to produce a retentate solution using one or more retentate access ports to supply gas and liquid to the retentate side of the stage 1 ultrafilter membrane.

26. The method of claim 10 wherein the retentate solution is collected from a retentate access port.

27. The method of claim 26 wherein the filtrate from the permeate side of the stage 1 ultrafilter membrane is flushed with gas using one or more permeate access ports to drain filtrate and supply gas to the permeate side of the stage 1 ultrafilter membrane.

28. The method of claim 26 wherein the retentate side of the stage 1 ultrafilter membrane is flushed with gas and with liquid to produce a retentate solution using one or more retentate access ports to supply gas and liquid to the retentate side of the stage 1 ultrafilter membrane.

\* \* \* \* \*